(12) United States Patent
McShea et al.

(10) Patent No.: US 12,076,436 B2
(45) Date of Patent: Sep. 3, 2024

(54) **BACTERIAL FERMENT OF *LACTOBACILLUS* SPECIES**

(71) Applicant: Symrise AG, Holzminden (DE)

(72) Inventors: Andrew McShea, Suquamish, WA (US); Katrina Nielsen, Redmond, WA (US); Joachim Hans, Holzminden (DE); Mirjam Knupfer, Holzminden (DE); Dominik Stuhlmann, Holzminden (DE); Imke Meyer, Bodenwerder (DE); Léa Schmidt, Courbevoie (FR); Marco Massironi, Padua (IT); Francesca Benato, Teolo (IT); Sandro Rosa, Padua (IT)

(73) Assignee: SYMRISE AG, Holzminden (DE)

( * ) Notice: Subject to any disclaimer, the term of this patent is extended or adjusted under 35 U.S.C. 154(b) by 35 days.

(21) Appl. No.: 17/737,206

(22) Filed: May 5, 2022

(65) Prior Publication Data
US 2022/0354775 A1    Nov. 10, 2022

Related U.S. Application Data

(60) Provisional application No. 63/185,489, filed on May 7, 2021.

(51) Int. Cl.
| | | |
|---|---|---|
| A61K 8/99 | (2017.01) | |
| A61K 35/74 | (2015.01) | |
| A61Q 5/02 | (2006.01) | |
| A61Q 5/12 | (2006.01) | |
| A61Q 15/00 | (2006.01) | |
| A61Q 19/00 | (2006.01) | |
| A61Q 19/08 | (2006.01) | |
| A61Q 19/10 | (2006.01) | |
| C12N 1/20 | (2006.01) | |

(52) U.S. Cl.
CPC .............. *A61K 8/99* (2013.01); *A61K 35/74* (2013.01); *A61Q 5/02* (2013.01); *A61Q 5/12* (2013.01); *A61Q 15/00* (2013.01); *A61Q 19/007* (2013.01); *A61Q 19/08* (2013.01); *A61Q 19/10* (2013.01); *C12N 1/20* (2013.01)

(58) Field of Classification Search
CPC ...................................................... A61K 8/99
See application file for complete search history.

(56) References Cited

FOREIGN PATENT DOCUMENTS

| CN | 1156481 A | 8/1997 |
| JP | S62100298 A | 5/1987 |
| WO | 2013153358 A1 | 10/2013 |
| WO | 2020182970 A1 | 9/2020 |

OTHER PUBLICATIONS

Kim H. et al: "Effect of paraprobiotic prepared from Kimchi-derived Lactobacillus plantarum KS on skin moisturizing activity in human keratinocyte", Journal of Functional Foods, vol. 75, 104244, Oct. 19, 2020 (Oct. 19, 2020), pp. 1-7, XPOS6395130, ISSN: 1756-4646, DOI: 10.1016/J.JFF.2020.104244 [retrieved on Oct. 19, 2020].
Kim B. s. et al: "Inhibitory Effect of Lipoteichoic Acid Derived from Three Lactobacilli on Flagellin-Induced IL-S Production in Porcine Peripheral Blood Mononuclear Cells", Robiotics and Antimicrobial Proteins, vol. 13, Jun. 30, 2020 (Jun. 30, 2020), pp. 72-79, XP0373S1204, ISSN: 1S67-1306, DOI: 10.1007/SI2602-020-096S2-3.
Boomsma B. et al: "L-Lactic Acid—A Safe Antimicrobial for Home- and Personal Care Formulations", SOFW Journal, vol. 141, Oct. 12, 2015 (Oct. 12, 2015), pp. 1-5, XP055S7S391.
Islam M. S. et al: "A Review on Macroscale and Microscale Cell Lysis Methods", Micromachines, vol. 8, 83, Mar. 8, 2017 (Mar. 8, 2017), pp. 1-27, XPOSSSSS969, DOI: 10.3390/mi8030083.
International search report and written opinion dated Jan. 5, 2022, for corresponding PCT/EP2021/072613.

*Primary Examiner* — Albert M Navarro
(74) *Attorney, Agent, or Firm* — Timothy H. Van Dyke; WOLTER, VAN DYKE, DAVIS, PLLC

(57) ABSTRACT

A bacterial ferment obtained by a method including the following steps: (a) culturing *Lactobacillus* species in at least one growth medium for at least 24 hours; (b) separating the mixture via centrifugation; (c) adding lactic acid to the supernatant obtained from step b) in an amount sufficient to lower the pH value of the supernatant; (d) stabilizing the resulting mixture with the addition of at least one preservative and/or at least one multifunctional; and optionally (e) filtering the mixture to remove any final precipitation.

4 Claims, 3 Drawing Sheets

BACTERIAL FERMENT OF *LACTOBACILLUS* SPECIES

CROSS REFERENCE TO RELATED APPLICATIONS

This application claims priority to U.S. Provisional Application No. 63/185,489 filed May 7, 2021, and to International Application No. PCT/EP2021/072613 filed Aug. 13, 2021, both of which are incorporated by reference herein in their entireties.

FIELD OF INVENTION

The invention relates to a bacterial ferment of *Lactobacillus* species, methods to obtain the bacterial ferment and its use in cosmetic and pharmaceutical applications.

BACKGROUND OF THE INVENTION

Lactic acid generating bacteria, as well as a large ecosystem of related organisms, are commercially important for food, human health care and industrial applications. Some of the best understood examples of the commercial value of lactic acid bacteria are related to their ability to preserve foods and milk products such as sauerkraut, yoghurt and cheese. Other applications include the fermentation of grasses to produce silage, a long-lasting and critical animal feedstuff for winters.

More recently specific mixtures of defined lactic acid bacteria have been consumed directly at high concentrations as probiotics. The use of probiotic supplementation is a newer approach to improving human health and affecting specific symptoms. The strategy being to influence the microbiome of the host, rather than intervening directly in host cell biochemistry with conventional drugs. This approach is coincident with the growing understanding that the commensal microbiome within humans (and indeed likely all organisms on earth) is a critical factor that influences the health of the host. The impact of the microbiome and the interaction of the microbiome with its host is not only limited to areas of the body with very high bacterial counts, such as the gut, but is also very important in any area where the human body encounters its environment such as the skin. With the growing trend toward less artificial or 'drug-like' chemistries for skin applications, the commercial potential for biotic approaches to cosmetics with products derived from probiotics is significant. As probiotics have an exceedingly long history of safe use, are not synthetic chemicals, and are themselves already components of the commensal microbiome they are viewed favourably by consumers.

Bacteria that generate simple acids, such as lactic acid, (hence lactic acid bacteria and the bacterial genus *Lactobacilli*) can acidify their surrounding environment by converting simple sugars into acids and lowering the pH to around 4. This is the simplest mechanism by which bacteria can control their environment, as a rapid drop in pH makes it harder for other organisms to compete, and hence 'spoil', the surrounding environment, or foodstuff. Lactic acid bacteria also have ability to control their environment by producing various types of compounds that act directly on the host organism or other bacteria by directly releasing biologically active molecules into the surrounding environment. These can be proteins, peptides, glycol-peptides, large complex polysaccharides, or other small molecules that exert their effects by mechanisms distinct to pH alteration. These secreted factors released into extracellular environment can also be generally described as a secretome and the functions of the secretome are generally thought to be related to 1) interacting with other organisms in the environment, (2) recognition, binding, degradation and uptake of extracellular complex nutrients, (3) signal transduction, (4) communication with the environment and (5) attachment of the bacterial cell to specific sites or surfaces, e.g. to intestinal mucosa cells of the host.

During the manufacturing process of any probiotic over 90% the growth media is usually discarded as the probiotic is separated from the growth media in a centrifugation process. The solid material separated by centrifugation is usually referred to as the probiotic, or a probiotic lysate if it is lyzed, a process commonly done for cosmetic applications. The growth media can be converted to a product usually known as a ferment within the art. Clearly the production of useful products from the growth media reflects an opportunity to increase the efficiency of manufacturing and limit waste production during manufacturing by converting the culture media that surrounds the trillions of live probiotics into products and hence reduce the overall cost of goods, even if subsequent downstream processing steps may add some additional cost.

This approach is not without commercial precedent as products that are based on the growth media from both lactic acid bacteria ferments as well as fermented yeasts exist or have been commercialized previously. *Lactobacillus ferment* is an established ingredient, recognized by the under the International Nomenclature of Cosmetic Ingredients (INCI). Another example is the Pitera product sold under the SK-II brand, a yeast ferment product. The marketing of the Pitera product highlights the safety, natural role in the fermentation process and the lack of preservatives.

There is a vast ecosystem of potential bacteria and other microorganisms such as yeast and fungi that could be used as the starting material to generate various types of ferments. Each of these microorganisms can generate ferments of very different specifications and each of these ferments may need to be produced in a specific manner to retain desired biological activities and ensure that the ferment is stable for its intended application.

However, the challenges in the production of any microbiological ferment are threefold: Firstly, the ferment is derived from growth media that supports the growth of a wide range of microorganisms. Therefore, the product is intrinsically microbially unstable unless specific processes are applied to prevent further growth of microorganisms and rapid spoilage of the ferment. During production spoilage is prevented and controlled by ensuring complete sterility of the growth media and using only precisely defined microbial inoculum that contains only the probiotic organisms and is free of contaminating micro-organisms. However, as the final ferment product is desired to be used in a wide range of commercial applications the bacterial growth media has to undergo additional processing to ensure that it is stable for its intended use and that the aesthetic characteristics of the product meet market needs.

Secondly, the aesthetic properties of the ferment need to be adjusted without the use of harsh chemicals. Adjustment of the colour and the odour of the bacterial growth medium is important for commercial viability as bacterial growth medium that has supported the growth of probiotics is often brown or dark brown and can have unpleasant or sulfurous odors. For cosmetic ingredient applications a lighter colour is desirable and for nearly any application in human use it is important to avoid unpleasant product odours.

Thirdly, the regulatory environment that governs the use of cosmetic ingredients generally requires that a product have a total bacterial count of 100 organisms per gram or less. At the time of production, a bacterial ferment typically has a bacterial count of over a trillion bacteria per gram. Therefore, to convert this material to a product that meets regulatory requirements for live bacteria requires a log fold reduction of viable count exceeding nine orders of magnitude. This is a major technical hurdle as nearly all sterilization techniques within the art commonly reduce bacterial counts by only fix to six orders of magnitude and most of the sterilization techniques employ chemical or physical processes that would damage the compounds released by the bacteria into their environment.

SUMMARY OF THE INVENTION

Accordingly, it is the object of the present invention to address the problems of product stability with bacterial ferment production whilst retaining maximum biological activity and avoiding the use of harsh chemicals or additives that may adversely affect product characteristics.

This object is solved by the claims according to the present invention. The present invention describes a bacterial ferment of *Lactobacillus* species obtained by a method comprising the steps of
(a) culturing *Lactobacillus* species in at least one growth medium for at least 24 hours;
(b) separating the mixture via centrifugation;
(c) adding lactic acid to the supernatant obtained from step b) in an amount sufficient to lower the pH value of the supernatant;
(d) stabilizing the resulting mixture with the addition of at least one preservative and/or at least one multifunctional; and
(e) optionally filtering the mixture to remove any final precipitation.

Surprisingly it has been found that it is possible with the method according to the present invention to obtain a bacterial ferment with minimal or not residual microbial count which retains biological activity of commercial value for cosmetic and human health applications.

Furthermore, it was found that the bacterial ferment obtained by the method of the present invention can be sterilized very effectively due to a short pH shock with lactic acid, which leads to an at least 9-order reduction in bacterial count (step c). For comparison, with conventional methods like heating or sterilization a 5 to 6-order reduction can be usually contained. However, this was very surprising, since *Lactobacilli* are expected to be resistant to lactic acid. Therefore, the bacterial ferment according to the present invention is still active, has desirable colour and a very low bacterial count.

The present invention further relates to a method for producing a bacterial ferment of *Lactobacillus* species, comprising the steps of
(a) culturing *Lactobacillus* species in at least one growth medium for at least 24 hours;
(b) separating the mixture via centrifugation;
(c) adding lactic acid to the supernatant obtained from step b) in an amount sufficient to lower the pH value of the supernatant;
(d) stabilizing the resulting mixture with the addition of at least one preservative; and optionally
(e) filtering the mixture to remove any final precipitation.

In a preferred embodiment according to the invention, the growth medium comprises a blend of yeast extract, yeast peptone, sodium acetate, dextrose, sucrose, ammonium citrate, potassium phosphate, ascorbic acid, L-cysteine, magnesium sulfate, tween-80 and/or water.

In a further preferred embodiment according to the invention, the mixture is combined with at least one other mixture of a different *Lactobacillus* species prepared with the same method of culturing, separating via centrifugation and adding of lactic acid before stabilizing the resulting mixture with the addition of at least one preservative, to produce a mixture of materials from different *Lactobacillus* species. This additional preferred step can be beneficial, since due to the combination different actives of different *Lactobacilli* strains are included in the bacterial ferment.

In a further preferred embodiment of the invention, the resulting mixture is stabilized with the addition of at least one multifunctional or multifunctional compound. Multifunctionals or multifunctional compounds are compounds or substances that enhance the performance of active ingredients, improves formula aesthetics including dispensability of pigments, stabilizes emulsions, act as solubilizer or moisturizer and also provide product protection. These multitaskers help to eliminate the overall number of ingredients while maximizing formula benefits and optimizing consumer experience. Multifunctionals or multifunctional compounds in the context of the present invention are preferably polyols respective glycols, such as 1,2-propanediol (propylene glycol), 1,3-propanediol, 1,2-butanediol, 1,3-butanediol (butylene glycol), 1,2-pentanediol (pentylene glycol; Hydrolite® 5; green version or any grade), 1,2-hexanediol (Hydrolite® 6), 1,2-heptanediol, 1,2-octanediol (caprylyl glycol; Hydrolite® 8), 1,2-nonanediol, 1,2-decanediol (decylene glycol), or glycerol, phenoxyethanol, ethylhexylglycerin, glyceryl caprylate, hydroxyacetophenone, methylbenzyl alcohol, o-cymen-5-ol, benzyl alcohol, tropolone, or mixtures of two or more of said multifunctionals, which are known compounds commonly used as ingredient in cosmetics or pharmaceutical preparetions.

From the above multifunctional ingredients, glycols that for example boosts the performance of active ingredients, improves the sensorial profile of formulas and enhances product protection, are particularly preferred.

Preferably, the multifunctional or the multifunctional compound according to the present invention is a polyol selected from the group consisting of 1,2-pentanediol (pentylene glycol; Hydrolite® 5; green version or any grade), 1,2-hexanediol (Hydrolite® 6), 1,2-heptanediol and 1,2-octanediol (caprylyl glycol; Hydrolite® 8).

Preferably a cosmetic or pharmaceutical preparation, according to the present invention can also contain active compounds for preservative purposes, wherein any preservatives may be used which are suitable or customary in cosmetic or pharmaceutical, in particular dermatological, applications. In a further preferred embodiment of the invention, the resulting mixture is stabilized with the addition of at least one preservative. The preservatives are advantageously selected from the group consisting of preservatives such as inter alia benzoic acid, its esters and salts; propionic acid and its salts; salicylic acid and its salts; 2,4-hexanoic acid (sorbic acid) and its salts; formaldehyde and paraformaldehyde; 2-hydroxybiphenyl ether and its salts; 2-zincsulphidopyridine N-oxide; inorganic sulphites and bisulphites; sodium iodate; chlorobutanol; 4-hydroxybenzoic acid and its salts and esters; dehydroacetic acid; formic acid; 1,6-bis (4-amidino-2-bromophenoxy)-n-hexane and its salts; the sodium salt of ethylmercury-(II)-thiosalicylic acid; phenylmercury and its salts; 10-undecylenic acid and its salts; 5-amino-1,3-bis(2-ethylhexyl)-5-methylhexahydropyrimidine; 5-bromo-5-nitro-1,3-dioxane; 2-bromo-2-nitro-1,3-propanediol; 2,4-dichlorobenzyl alcohol; N-(4-chlorophenyl)-N'-(3,4-dichlorophenyl)urea; 4-chloro-m-cresol; 2,4,4'-trichloro-2'-hydroxy-diphenyl ether; 4-chloro-3,5-dimethylphenol; 1,1'-methylene-bis(3-(1-hydroxymethyl-2,4-dioximidazolidin-5-yl)urea); poly(hexamethylene biguanide) hydrochloride; 2-phenoxyethanol; hexamethylene-tetramine; 1-(3-chloroallyl)-3,5,7-triaza-1-azoniaadamantane chloride; 1-(4-chloro-phenoxy)-1 (1H-imidazol-1-yl)-3,3-dimethyl-2-butanone; 1,3-bis(hydroxymethyl)-5,5-dimethyl-2,4-imidazolidinedione; benzyl alcohol; Octopirox®; 1,2-dibromo-2,4-dicyanobutane; 2,2'-methylene-bis(6-bromo-4-chloro-phenol); bromochlorophene; mixture of 5-chloro-2-methyl-3(2H)-isothiazolinone and 2-methyl-3(2H)isothiazolinone with magnesium chloride and magnesium nitrate; 2-benzyl-4-chlorophenol; 2-chloroacetamide; chlorhexidine; chlorhexidine acetate; chlorhexidine gluconate; chlorhexidine hydrochloride; 1-phenoxypropan-2-ol; N-alkyl(C12-C22)trimethylammonium bromide and chloride; 4,4-dimethyl-1,3-oxazolidine; N-hydroxymethyl-N-(1,3-di(hydroxymethyl)-2,5-dioxoimidazolidin-4-yl)-N'-hydroxymethylurea; 1,6-bis(4-amidinophenoxy)-n-hexane and its salts; glutaraldehyde 5-ethyl-1-aza-3,7-dioxabicyclo(3.3.0)octane; 3-(4-chlorophenoxy)-1,2-propanediol; hyamine; alkyl(C8-C18) dimethylbenzylammonium chloride; alkyl(C8-C18) dimethylbenzylammonium bromide; alkyl(C8-C18) dimethylbenzylammonium saccharinate; benzylhemiformal; 3-iodo-2-propynyl butylcarbamate; sodium ((hydroxymethyl)amino)acetate.

As the taxonomy of this genus (*Lactobacillus*) has recently been altered by the Taxonomic Subcommittee, (the scientific organization responsible for the nomenclature of *Lactobacilli*) the invention refers also to any of the follow genera: *Lactobacillus, Lactobacillus delbrueckii* group, *Paralactobacillus, Holzapfelia, Amylolactobacillus, Bombilactobacillus, Companilactobacillus, Lapidilactobacillus, Agrilactobacillus, Schleiferilactobacillus, Loigolactobacillus, Lacticaseibacillus, Latilactobacillus, Dellaglioa, Liquorilactobacillus, Ligilactobacillus, Lactiplantibacillus, Furfurilactobacillus, Paucilactobacillus, Limosilactobacillus, Fructilactobacillus, Acetilactobacillus, Apilactobacillus, Levilactobacillus, Secundilactobacillus* and *Lentilactobacillus*.

In a further preferred embodiment according to the invention, the *Lactobacillus* species is selected from the group consisting of *Lactobacillus acidophilus, Lactobacillus casei, Lactobacillus fermentum, Lactobacillus gasseri, Lactobacillus helveticus, Lactobacillus paracasei, Lactobacillus plantarum, Lactobacillus reuteri, Lactobacillus rhamnosus, Lactobacillus sakei* and *Lactobacillus salivarius*.

Preferably, lactic acid is added in an amount of from 2 to 10 percent by weight, based on the total amount of the mixture. More preferably, lactic acid is added in an amount of from 4 to 7 percent by weight, based on the total amount of the mixture.

Preferably, the method according to the present invention comprises the following steps:
(a) culturing *Lactobacillus* species in at least one growth medium for at least 24 hours;
(b) separating the mixture via centrifugation;
(c) adding lactic acid to the supernatant obtained from step b) in an amount sufficient to lower the pH value of the supernatant;
(d) adding solid and/or aqueous sodium benzoate to the resulting mixture;
(e) incubating the mixture for at least 12 hours;
(f) stabilizing the resulting mixture with the addition of at least one preservative and/or at least one multifunctional; and optionally
(g) filtering the mixture to remove any final precipitation.

More preferably, the method according to the present invention comprises the following steps:
(a) culturing *Lactobacillus* species in at least one growth medium for at least 24 hours;
(b) separating the mixture via centrifugation;
(c) adding lactic acid to the supernatant obtained from step b) in an amount sufficient to lower the pH value of the supernatant;
(d) adding solid and/or aqueous sodium benzoate to the resulting mixture;
(e) incubating the mixture for at least 12 hours;
(f) passing the mixture through a carbon filter:
(g) stabilizing the resulting mixture with the addition of at least one preservative and/or at least one multifunctional; and optionally
(h) filtering the mixture to remove any final precipitation.

In a preferred embodiment according to the invention, the carbon filter is an activated and/or catalytic carbon filter. More preferably, the method according to the present invention comprises or consists of the following steps:
(a) culturing *Lactobacillus* species in at least one growth medium for at least 24 hours;
(b) separating the mixture via centrifugation;
(c) adding lactic acid to the supernatant obtained from step b) in an amount sufficient to lower the pH value of the supernatant;
(d) adding solid and/or aqueous sodium benzoate to the resulting mixture; optionally
(e) combining the mixture with at least one other mixture of a different *Lactobacillus species prepared with the same method of culturing, separating via centrifugation and adding of lactic acid and/or solid and/or aqueous sodium benzoate;*
(f) analyzing the mixture to measure bacterial counts and the pH value;
(g) incubating the mixture for at least 12 hours;
(h) passing the mixture through a carbon filter:
(i) stabilizing the resulting mixture with the addition of at least one preservative and/or at least one multifunctional;
(j) adjusting the pH value with the addition of a suitable amount of ammonium hydroxide; and optionally
filtering and/or separating the mixture via centrifugation to remove any final precipitation In a preferred embodiment according to the invention, adding of lactic acid to the mixture results in a pH shock which produces a 9-order reduction in bacterial count. A pH shock in the sense of the invention is a rapid change of the pH of mixture within a short period of time. Preferably, the pH value is lowered by 0.5 to 4.5, more preferably by 1 to 4, most preferably by 2 to 3.5. In a preferred embodiment according to the invention, the initial pH value before adding lactic acid is about 5 to 7, preferably about 5.5 to 6.5.

Cosmetic and/or Pharmaceutical Compositions

According to a further aspect, the invention also relates to a pharmaceutical or cosmetic composition or pharmaceutical or cosmetic product comprising the bacterial ferment, in a working amount, for example about 0.1 to about 10 wt.-percent, preferably about 0.5 to about 8 wt.-percent and particularly from about 1 to about 5 wt.-percent—calculated on the composition(s). The composition may represent for example a cosmetic cream, lotion, spray, emulsion, ointment, gel or mouse and the like.

The preparations according to the invention may contain antidandruff agents, irritation-preventing agents, irritation-inhibiting agents, antioxidants, adstringents, perspiration-inhibiting agents, antiseptic agents, ant-statics, binders, buffers, carrier materials, chelating agents, cell stimulants, cleansing agents, care agents, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, hair promotion agents, cooling agents, skin-cooling agents, warming agents, skin-warming agents, stabilizers, UV-absorbing agents, UV filters, detergents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Non-ionic and cationic surfactants can be also present in the composition. Suitable examples are mentioned along with the paragraph dealing with emulsifiers.

Typical examples for anionic and zwitterionic surfactants encompass: Almondamidopropylamine Oxide, Almondamidopropyl Betaine, Aminopropyl Laurylglutamine, Ammonium C12-15 Alkyl Sulfate, Ammonium C12-16 Alkyl Sulfate, Ammonium Capryleth Sulfate, Ammonium Cocomonoglyceride Sulfate, Ammonium Coco-Sulfate, Ammonium Cocoyl Isethionate, Ammonium Cocoyl Sarcosinate, Ammonium C12-15 Pareth Sulfate, Ammonium C9-10 Perfluoroalkylsulfonate, Ammonium Dinonyl Sulfosuccinate, Ammonium Dodecylbenzenesulfonate, Ammonium Isostearate, Ammonium Laureth-6 Carboxylate, Ammonium Laureth-8 Carboxylate, Ammonium Laureth Sulfate, Ammonium Laureth-5 Sulfate, Ammonium Laureth-7 Sulfate, Ammonium Laureth-9 Sulfate, Ammonium Laureth-12 Sulfate, Ammonium Lauroyl Sarcosinate, Ammonium Lauryl Sulfate, Ammonium Lauryl Sulfosuccinate, Ammonium Myreth Sulfate, Ammonium Myristyl Sulfate, Ammonium Nonoxynol-4 Sulfate, Ammonium Nonoxynol-30 Sulfate, Ammonium Oleate, Ammonium Palm Kernel Sulfate, Ammonium Stearate, Ammonium Tallate, AMPD-Isostearoyl Hydrolyzed Collagen, AM PD-Rosin Hydrolyzed Collagen, AMP-Isostearoyl Hydrolyzed Collagen, AMP-Isostearoyl Hydrolyzed Keratin, AMP-Isostearoyl Hydrolyzed Soy Protein, AMP-Isostearoyl Hydrolyzed Wheat Protein, Apricotamidopropyl Betaine, Arachidic Acid, Arginine Hexyldecyl Phosphate, Avocadamidopropyl Betaine, Avocado Oil Glycereth-8 Esters, Babassu Acid, Babassuamidopropylamine Oxide, Babassuamidopropyl Betaine, Beeswax Acid, Behenamidopropyl Betaine, Behenamine Oxide, Beheneth-25, Beheneth-30, Behenic Acid, Behenyl Betaine, Bis-Butyldimethicone Polyglyceryl-3, Butoxynol-5 Carboxylic Acid, Butoxynol-19 Carboxylic Acid, Butyldimoniumhydroxypropyl Butylglucosides Chloride, Butyldimoniumhydroxypropyl Laurylglucosides Chloride, Butyl Glucoside, Butylglucoside Caprate, Butylglucosides Hydroxypropyltrimonium Chloride, Butyloctanoic Acid, C18-36 Acid, C20-40 Acid, C30-50 Acid, C16-22 Acid Amide MEA, Calcium Dodecylbenzenesulfonate, Calcium Lauroyl Taurate, C9-16 Alkane/Cycloalkane, C10-14 Alkyl Benzenesulfonic Acid, C12-14 Alkyl Diaminoethylglycine HCL, C9-15 Alkyl Phosphate, Candida Bombicola/Glucose/Methyl Rapeseedate Ferment, Canolamidopropyl Betaine, Capric Acid, Caproic Acid, Caproyl Ethyl Glucoside, Capryl/Capramidopropyl Betaine, Capryleth-4 Carboxylic Acid, Capryleth-6 Carboxylic Acid, Capryleth-9 Carboxylic Acid, Caprylic Acid, Capryloyl Collagen Amino Acids, Capryloyl Glycine, Capryloyl Hydrolyzed Collagen, Capryloyl Hydrolyzed Keratin, Capryloyl Keratin Amino Acids, Capryloyl Silk Amino Acids, Caprylyl/Capryl Glucoside, Caprylyl/Capryl Wheat Bran/Straw Glycosides, Caprylyl Glucoside, Caprylyl Glyceryl Ether, Caprylyl Pyrrolidone, Carnitine, Ceteareth-20, Ceteareth-23, Ceteareth-24, Ceteareth-25, Ceteareth-27, Ceteareth-28, Ceteareth-29, Ceteareth-30, Ceteareth-33, Ceteareth-34, Ceteareth-40, Ceteareth-50, Ceteareth-55, Ceteareth-60, Ceteareth-80, Ceteareth-100, Ceteareth-25 Carboxylic Acid, Ceteareth-2 Phosphate, Ceteareth-4 Phosphate, Ceteareth-5 Phosphate, Ceteareth-10 Phosphate, Ceteth-20, Ceteth-23, Ceteth-24, Ceteth-25, Ceteth-30, Ceteth-40, Ceteth-45, Ceteth-150, Ceteth-8 Phosphate, Ceteth-10 Phosphate, Ceteth-20 Phosphate, Cetoleth-22, Cetoleth-24, Cetoleth-25, Cetoleth-30, Cetyl Betaine, Chrysanthemum Sinense Flower Extract, C12-14 Hydroxyalkyl Hydroxyethyl Beta-Alanine, C12-14 Hydroxyalkyl Hydroxyethyl Sarcosine, Cocamidoethyl Betaine, Cocamidopropylamine Oxide, Cocamidopropyl Betainamide MEA Chloride, Cocamidopropyl Betaine, Cocamidopropyl Hydroxysultaine, Cocamine Oxide, Cocaminobutyric Acid, Cocaminopropionic Acid, Coceth-7 Carboxylic Acid, Coceth-4 Glucoside, Cocoamphodipropionic Acid, Cocobetainamido Amphopropionate, Coco-Betaine, Cocodimonium Hydroxypropyl Hydrolyzed Rice Protein, Cocodimonium Hydroxypropyl Hydrolyzed Soy Protein, Cocodimonium Hydroxypropyl Hydrolyzed Wheat Protein, Coco-Glucoside, Cocoglucosides Hydroxypropyltrimonium Chloride, Coco-Hydroxysultaine, Coco-Morpholine Oxide, Coconut Acid, Coconut Oil Glycereth-8 Esters, Coco/Oleamidopropyl Betaine, Coco-Sultaine, Coco/Sunfloweramidopropyl Betaine, Cocoylcholine Methosulfate, Cocoyl Glutamic Acid, Cocoyl Hydrolyzed Collagen, Cocoyl Hydrolyzed Keratin, Cocoyl Hydrolyzed Oat Protein, Cocoyl Hydrolyzed Rice Protein, Cocoyl Hydrolyzed Silk, Cocoyl Hydrolyzed Soy Protein, Cocoyl Hydrolyzed Wheat Protein, Cocoyl Sarcosine, Corn Acid, Cottonseed Acid, Cottonseed Oil Glycereth-8 Esters, C10-16 Pareth-1, C10-16 Pareth-2, C11-13 Pareth-6, C11-13 Pareth-9, C11-13 Pareth-10, C11-15 Pareth-30, C11-15 Pareth-40, C12-13 Pareth-1, C12-13 Pareth-23, C12-14 Pareth-5, C12-14 Pareth-9, C13-15 Pareth-21, C14-15 Pareth-8, C20-22 Pareth-30, C20-40 Pareth-40, C20-40 Pareth-95, C22-24 Pareth-33, C30-50 Pareth-40, C9-11 Pareth-6 Carboxylic Acid, C9-11 Pareth-8 Carboxylic Acid, C11-15 Pareth-7 Carboxylic Acid, C12-13 Pareth-5 Carboxylic Acid, C12-13 Pareth-7 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C12-15 Pareth-12 Carboxylic Acid, C14-15 Pareth-8 Carboxylic Acid, C6-10 Pareth-4 Phosphate, C12-13 Pareth-2 Phosphate, C12-13 Pareth-10 Phosphate, C12-15 Pareth-6 Phosphate, C12-15 Pareth-8 Phosphate, C12-15 Pareth-10 Phosphate, C12-16 Pareth-6 Phosphate, C4-18

Perfluoroalkylethyl Thiohydroxypropyltrimonium Chloride, Cupuassuamidopropyl Betaine, DEA-C12-13 Alkyl Sulfate, DEA-C12-15 Alkyl Sulfate, DEA-Ceteareth-2 Phosphate, DEA-Cetyl Sulfate, DEA-Cocoamphodipropionate, DEA-C12-13 Pareth-3 Sulfate, DEA-Cyclocarboxypropyloleate, DEA-Dodecylbenzene-sulfonate, DEA-Isostearate, DEA-Laureth Sulfate, DEA-Lauryl Sulfate, DEA-Linoleate, DEA-Methyl Myristate Sulfonate, DEA-Myreth Sulfate, DEA-Myristate, DEA-Myristyl Sulfate, DEA-Oleth-5 Phosphate, DEA-Oleth-20 Phosphate, DEA PG-Oleate, Deceth-7 Carboxylic Acid, Deceth-7 Glucoside, Deceth-9 Phosphate, Decylamine Oxide, Decyl Betaine, Decyl Glucoside, Decyltetradeceth-30, Decyltetradecylamine Oxide, Diammonium Lauramido-MEA Sulfosuccinate, Diammonium Lauryl Sulfosuccinate, Diammonium Oleamido PEG-2 Sulfosuccinate, Dibutoxymethane, Di-C1 2-15 Pareth-2 Phosphate, Di-C1 2-15 Pareth-4 Phosphate, Di-C1 2-15 Pareth-6 Phosphate, Di-C12-15 Pareth-8 Phosphate, Di-C1 2-15 Pareth-10 Phosphate, Didodecyl Butanetetracarboxylate, Diethylamine Laureth Sulfate, Diethylhexyl Sodium Sulfosuccinate, Dihydroxyethyl C8-10 Alkoxypropylamine Oxide, Dihydroxyethyl C9-11 Alkoxypropylamine Oxide, Dihydroxyethyl C12-15 Alkoxypropylamine Oxide, Dihydroxyethyl Cocamine Oxide, Dihydroxyethyl Lauramine Oxide, Dihydroxyethyl Stearamine Oxide, Dihydroxyethyl Tallowamine Oxide, Dimethicone PEG-7 Phosphate, Dimethicone PEG-10 Phosphate, Dimethicone PEG/PPG-7/4 Phosphate, Dimethicone PEG/PPG-12/4 Phosphate, Dimethicone/Polyglycerin-3 Crosspolymer, Dimethicone Propyl PG-Betaine, Dimyristyl Phosphate, Dioleoylamidoethyl Hydroxyethylmonium Methosulfate, DIPA-Hydrogenated Cocoate, DIPA-Lanolate, DIPA-Myristate, Dipotassium Capryloyl Glutamate, Dipotassium Lauryl Sulfosuccinate, Dipotassium Undecylenoyl Glutamate, Disodium Babassuamido MEA-Sulfosuccinate, Disodium Caproamphodiacetate, Disodium Caproamphodipropionate, Disodium Capryloamphodiacetate, Disodium Capryloamphodipropionate, Disodium Capryloyl Glutamate, Disodium Cetearyl Sulfosuccinate, Disodium Cetyl Phenyl Ether Disulfonate, Disodium Cetyl Sulfosuccinate, Disodium Cocamido MEA-Sulfosuccinate, Disodium Cocamido MIPA PEG-4 Sulfosuccinate, Disodium Cocamido MIPA-Sulfosuccinate, Disodium Cocamido PEG-3 Sulfosuccinate, Disodium Coceth-3 Sulfosuccinate, Disodium Cocoamphocarboxyethylhydroxypropyl-sulfonate, Disodium Cocoamphodiacetate, Disodium Cocoamphodipropionate, Disodium Coco-Glucoside Sulfosuccinate, Disodium Coco-Sulfosuccinate, Disodium Cocoyl Butyl Gluceth-10 Sulfosuccinate, Disodium Cocoyl Glutamate, Disodium C12-14 Pareth-1 Sulfosuccinate, Disodium C12-14 Pareth-2 Sulfosuccinate, Disodium C12-15 Pareth Sulfosuccinate, Disodium C12-14 Sec-Pareth-3 Sulfosuccinate, Disodium C12-14 Sec-Pareth-5 Sulfosuccinate, Disodium C12-14 Sec-Pareth-7 Sulfosuccinate, Disodium C12-14 Sec-Pareth-9 Sulfosuccinate, Disodium C12-14 Sec-Pareth-12 Sulfosuccinate, Disodium Deceth-5 Sulfosuccinate, Disodium Deceth-6 Sulfosuccinate, Disodium Decyl Phenyl Ether Disulfonate, Disodium Dihydroxyethyl Sulfosuccinylundecylenate, Disodium Ethylene Dicocamide PEG-15 Disulfate, Disodium Hydrogenated Cottonseed Glyceride Sulfosuccinate, Disodium Hydrogenated Tallow Glutamate, Disodium Hydroxydecyl Sorbitol Citrate, Disodium Isodecyl Sulfosuccinate, Disodium Isostearamido MEA-Sulfosuccinate, Disodium Isostearamido MIPA-Sulfosuccinate, Disodium Isostearoamphodiacetate, Disodium Isostearoamphodipropionate, Disodium Isostearyl Sulfosuccinate, Disodium Laneth-5 Sulfosuccinate, Disodium Lauramido MEA-Sulfosuccinate, Disodium Lauramido MIPA Glycol Sulfosuccinate, Disodium Lauramido PEG-2 Sulfosuccinate, Disodium Lauramido PEG-5 Sulfosuccinate, Disodium Laureth-5 Carboxyamphodiacetate, Disodium Laureth-7 Citrate, Disodium Laureth Sulfosuccinate, Disodium Laureth-6 Sulfosuccinate, Disodium Laureth-9 Sulfosuccinate, Disodium Laureth-12 Sulfosuccinate, Disodium Lauriminobishydroxypropylsulfonate, Disodium Lauriminodiacetate, Disodium Lauriminodipropionate, Disodium Lauriminodipropionate Tocopheryl Phosphates, Disodium Lauroamphodiacetate, Disodium Lauroamphodipropionate, Disodium N-Lauroyl Aspartate, Disodium Lauroyl Glutamate, Disodium Lauryl Phenyl Ether Disulfonate, Disodium Lauryl Sulfosuccinate, Disodium Myristamido MEA-Sulfosuccinate, Disodium Nonoxynol-10 Sulfosuccinate, Disodium Oleamido MEA-Sulfosuccinate, Disodium Oleamido MIPA-Sulfosuccinate, Disodium Oleamido PEG-2 Sulfosuccinate, Disodium Oleoamphodipropionate, Disodium Oleth-3 Sulfosuccinate, Disodium Oleyl Phosphate, Disodium Oleyl Sulfosuccinate, Disodium Palmitamido PEG-2 Sulfosuccinate, Disodium Palmitoleamido PEG-2 Sulfosuccinate, Disodium PEG-4 Cocamido MIPA-Sulfosuccinate, Disodium PEG-12 Dimethicone Sulfosuccinate, Disodium PEG-8 Palm Glycerides Sulfosuccinate, Disodium PPG-2-lsodeceth-7 Carboxyamphodiacetate, Disodium Ricinoleamido MEA-Sulfosuccinate, Disodium Sitostereth-14 Sulfosuccinate, Disodium Soyamphodiacetate, Disodium Stearamido MEA-Sulfosuccinate, Disodium Steariminodipropionate, Disodium Stearoamphodiacetate, Disodium Stearoyl Glutamate, Disodium Stearyl Sulfosuccinamate, Disodium Stearyl Sulfosuccinate, Disodium 2-Sulfolaurate, Disodium 2-Sulfopalmitate, Disodium Tallamido MEA-Sulfosuccinate, Disodium Tallowamido MEA-Sulfosuccinate, Disodium Tallowamphodiacetate, Disodium Tallowiminodipropionate, Disodium Tallow Sulfosuccinamate, Disodium Tridecylsulfosuccinate, Disodium Undecylenamido MEA-Sulfosuccinate, Disodium Undecylenamido PEG-2 Sulfosuccinate, Disodium Undecylenoyl Glutamate, Disodium Wheat Germamido MEA-Sulfosuccinate, Disodium Wheat Germamido PEG-2 Sulfosuccinate, Disodium Wheatgermamphodiacetate, Di-TEA-Cocamide Diacetate, Di-TEA-Oleamido PEG-2 Sulfosuccinate, Di-TEA-Palmitoyl Aspartate, Ditridecyl Sodium Sulfosuccinate, Dodecylbenzene Sulfonic Acid, Erucamidopropyl Hydroxysultaine, Ethylhexeth-3 Carboxylic Acid, Ethyl PEG-15 Cocamine Sulfate, Glyceryl Capryl Ether, Hexyldecanoic Acid, Hydrogenated Coconut Acid, Hydrogenated Laneth-25, Hydrogenated Menhaden Acid, Hydrogenated Palm Acid, Hydrogenated Palm Kernel Amine Oxide, Hydrogenated Tallow Acid, Hydrogenated Tallowamine Oxide, Hydrogenated Tallow Betaine, Hydrogenated Talloweth-25, Hydrogenated Tallowoyl Glutamic Acid, Hydrolyzed Candida Bombicola Extract, Hydroxyceteth-60, Hydroxyethyl Acetomonium PG-Dimethicone, Hydroxyethylbutylamine Laureth Sulfate, Hydroxyethyl Carboxymethyl Cocamidopropylamine, Hydroxyethyl Hydroxypropyl C12-15 Alkoxypropylamine Oxide, Hydroxylauryl/Hydroxymyristyl Betaine, Hydroxystearic Acid, Hydroxysuccinimidyl C10-40 Isoalkyl Acidate, Hydroxysuccinimidyl C21-22 Isoalkyl Acidate, Hydroxysultaines, IPDI/PEG-15 Soyamine Oxide Copolymer, IPDI/PEG-15 Soyethonium Ethosulfate Copolymer, IPDI/PEG-15 Soy Glycinate Copolymer, lsoceteth-30, Isolaureth-4 Phosphate, Isopolyglyceryl-3 Dimethicone, Isopolyglyceryl-3 Dimethiconol, Isopropanolamine Lanolate, Isopropylamine Dodecylbenzenesulfonate, Isostearamidopropylamine Oxide, Isostearamidopropyl Betaine, Isostearamidopropyl Morpholine Oxide, Isosteareth-8, lsosteareth-16, Isosteareth-22, Isosteareth-25, Isosteareth-50, Isostearic Acid, Isostearoyl Hydrolyzed Collagen, Jojoba Oil PEG-150 Esters, Jojoba Wax PEG-80 Esters, Jojoba Wax PEG-120 Esters, Laneth-20, Laneth-25, Laneth-40, Laneth-50, Laneth-60, Laneth-75, Lanolin Acid, Lauramidopropylamine Oxide, Lauramidopropyl Betaine, Lauramidopropyl Hydroxysultaine, Lauramine Oxide, Lauraminopropionic Acid, Laurdimoniumhydroxypropyl Decylglucosides Chloride, Laurdimoniumhydroxypropyl Laurylglucosides Chloride, Laureth-16, Laureth-20, Laureth-21, Laureth-23, Laureth-25, Laureth-30, Laureth-38, Laureth-40, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, Laureth-6 Citrate, Laureth-7 Citrate, Laureth-1 Phosphate, Laureth-2 Phosphate, Laureth-3 Phosphate, Laureth-4 Phosphate, Laureth-7 Phosphate, Laureth-8 Phosphate, Laureth-7 Tartrate, Laurie Acid, Laurimino Bispropanediol, Lauriminodipropionic Acid, Lauroamphodipropionic Acid, Lauroyl Beta-Alanine, Lauroyl Collagen Amino Acids, Lauroyl Ethyltrimonium Methosulfate, Lauroyl Hydrolyzed Collagen, Lauroyl Hydrolyzed Elastin, Lauroyl Methyl Glucamide, Lauroyl Sarcosine, Lauroyl Silk Amino Acids, Lauryl Betaine, Lauryl Dimethicone/Polyglycerin-3 Crosspolymer, Lauryldimoniumhydroxypropyl Cocoglucosides Chloride, Lauryl Glucoside, Laurylglucosides Hydroxypropyltrimonium Chloride, Lauryl Glycol Hydroxypropyl Ether, Lauryl Hydroxysultaine, Lauryl Malamide, Lauryl Methylglucamide, Lauryl/Myristyl Glycol Hydroxypropyl Ether, Lauryl/Myristyl Wheat Bran/Straw Glycosides, Lauryl Polyglyceryl-3 Polydimethylsiloxyethyl Dimethicone, Lauryl Pyrrolidone, Lauryl Sultaine, Linoleic Acid, Linolenic Acid, Linseed Acid, Lysine Cocoate, Macadamia Seed Oil Glycereth-8 Esters, Magnesium Coceth Sulfate, Magnesium Coco-Sulfate, Magnesium Isododecylbenzene-sulfonate, Magnesium Laureth-11 Carboxylate, Magnesium Laureth Sulfate, Magnesium Laureth-5 Sulfate, Magnesium Laureth-8 Sulfate, Magnesium Laureth-16 Sulfate, Magnesium Laureth-3 Sulfosuccinate, Magnesium Lauryl Hydroxypropyl Sulfonate, Magnesium Lauryl Sulfate, Magnesium Methyl Cocoyl Taurate, Magnesium Myreth Sulfate, Magnesium Oleth Sulfate, Magnesium/TEA-Coco-Sulfate, Manicouagan Clay, MEA-Cocoate, MEA-Laureth-6 Carboxylate, MEA-Laureth Sulfate, MEA-Lauryl Sulfate, MEA PPG-6 Laureth-7 Carboxylate, MEA-PPG-8-Steareth-7 Carboxylate, MEA-Undecylenate, Meroxapol 108, Meroxapol 174, Meroxapol 178, Meroxapol 254, Meroxapol 255, Meroxapol 258, Meroxapol 314, Methoxy PEG-450 Amidoglutaroyl Succinimide, Methoxy PEG-450 Amido Hydroxysuccinimidyl Succinamate, Methoxy PEG-450 Maleimide, Methyl Morpholine Oxide, Milkamidopropyl Amine Oxide, Milkamidopropyl Betaine, Minkamidopropylamine Oxide, Minkamidopropyl Betaine, MIPA C12-15 Pareth Sulfate, MIPA-Dodecylbenzenesulfonate, MIPA-Laureth Sulfate, MIPA-Lauryl Sulfate, Mixed Isopropanolamines Lanolate, Mixed Isopropanolamines Lauryl Sulfate, Mixed Isopropanolamines Myristate, Morpholine Oleate, Morpholine Stearate, Myreth-3 Carboxylic Acid, Myreth-5 Carboxylic Acid, Myristalkonium Chloride, Myristamidopropylamine Oxide, Myristamidopropyl Betaine, Myristamidopropyl Dimethylamine Phosphate, Myristamidopropyl Hydroxysultaine, Myristamidopropyl PG-Dimonium Chloride Phosphate, Myristamine Oxide, Myristaminopropionic Acid, Myristic Acid, Myristoyl Ethyltrimonium Methosulfate, Myristoyl Glutamic Acid, Myristoyl Hydrolyzed Collagen, Myristoyl Sarcosine, Myristyl Betaine, Myristyl/Cetyl Amine Oxide, Myristyldimoniumhydroxypropyl Cocoglucosides Chloride, Myristyl Glucoside, Myristyl Phosphate, Nonoxynol-20, Nonoxynol-23, Nonoxynol-25, Nonoxynol-30, Nonoxynol-35, Nonoxynol-40, Nonoxynol-44, Nonoxynol-50, Nonoxynol-100, Nonoxynol-120, Nonoxynol-5 Carboxylic Acid, Nonoxynol-8 Carboxylic Acid, Nonoxynol-10 Carboxylic Acid, Nonoxynol-3 Phosphate, Nonoxynol-4 Phosphate, Nonoxynol-6 Phosphate, Nonoxynol-9 Phosphate, Nonoxynol-10 Phosphate, Nonyl Nonoxynol-30, Nonyl Nonoxynol-49, Nonyl Nonoxynol-100, Nonyl Nonoxynol-150, Nonyl Nonoxynol-7 Phosphate, Nonyl Nonoxynol-8 Phosphate, Nonyl Nonoxynol-9 Phosphate, Nonyl Nonoxynol-10 Phosphate, Nonyl Nonoxynol-11 Phosphate, Nonyl Nonoxynol-15 Phosphate, Nonyl Nonoxynol-24 Phosphate, Oatamidopropyl Betaine, Octoxynol-16, Octoxynol-25, Octoxynol-30, Octoxynol-33, Octoxynol-40, Octoxynol-70, Octoxynol-20 Carboxylic Acid, Octyldodeceth-20, Octyldodeceth-25, Octyldodeceth-30, Oleamidopropylamine Oxide, Oleamidopropyl Betaine, Oleamidopropyl Hydroxysultaine, Oleamine Oxide, Oleic Acid, Oleoyl Hydrolyzed Collagen, Oleoyl Sarcosine, Oleth-20, Oleth-23, Oleth-24, Oleth-25, Oleth-30, Oleth-35, Oleth-40, Oleth-44, Oleth-50, Oleth-3 Carboxylic Acid, Oleth-6 Carboxylic Acid, Oleth-10 Carboxylic Acid, Oleyl Betaine, Olivamidopropylamine Oxide, Olivamidopropyl Betaine, Olive Acid, Olivoyl Hydrolyzed Wheat Protein, Ophiopogon Extract Stearate, Ozonized Oleth-10, Ozonized PEG-10 Oleate, Ozonized PEG-14 Oleate, Ozonized Polysorbate 80, Palm Acid, Palmamidopropyl Betaine, Palmeth-2 Phosphate, Palmitamidopropylamine Oxide, Palmitamidopropyl Betaine, Palmitamine Oxide, Palmitic Acid, Palmitoyl Collagen Amino Acids, Palmitoyl Glycine, Palmitoyl Hydrolyzed Collagen, Palmitoyl Hydrolyzed Milk Protein, Palmitoyl Hydrolyzed Wheat Protein, Palmitoyl Keratin Amino Acids, Palmitoyl Oligopeptide, Palmitoyl Silk Amino Acids, Palm Kernel Acid, Palm Kernelamidopropyl Betaine, Peach Kernel Oil Glycereth-8 Esters, Peanut Acid, PEG-10 Castor Oil, PEG-40 Castor Oil, PEG-44 Castor Oil, PEG-50 Castor Oil, PEG-54 Castor Oil, PEG-55 Castor Oil, PEG-60 Castor Oil, PEG-80 Castor Oil, PEG-100 Castor Oil, PEG-200 Castor Oil, PEG-11 Cocamide, PEG-6 Cocamide Phosphate, PEG-4 Cocamine, PEG-8 Cocamine, PEG-12 Cocamine, PEG-150 Dibehenate, PEG-90 Diisostearate, PEG-75 Dilaurate, PEG-150 Dilaurate, PEG-75 Dioleate, PEG-150 Dioleate, PEG-75 Distearate, PEG-120 Distearate, PEG-150 Distearate, PEG-175 Distearate, PEG-190 Distearate, PEG-250 Distearate, PEG-30 Glyceryl Cocoate, PEG-40 Glyceryl Cocoate, PEG-78 Glyceryl Cocoate, PEG-80 Glyceryl Cocoate, PEG-30 Glyceryl Isostearate, PEG-40 Glyceryl Isostearate, PEG-50 Glyceryl Isostearate, PEG-60 Glyceryl Isostearate, PEG-90 Glyceryl Isostearate, PEG-23 Glyceryl Laurate, PEG-30 Glyceryl Laurate, PEG-25 Glyceryl Oleate, PEG-30 Glyceryl Oleate, PEG-30 Glyceryl Soyate, PEG-25 Glyceryl Stearate, PEG-30 Glyceryl Stearate, PEG-40 Glyceryl Stearate, PEG-120 Glyceryl Stearate, PEG-200 Glyceryl Stearate, PEG-28 Glyceryl Tallowate, PEG-80 Glyceryl Tallowate, PEG-82 Glyceryl Tallowate, PEG-130 Glyceryl Tallowate, PEG-200 Glyceryl Tallowate, PEG-45 Hydrogenated Castor Oil, PEG-50 Hydrogenated Castor Oil, PEG-54 Hydrogenated Castor Oil, PEG-55 Hydrogenated Castor Oil, PEG-60 Hydrogenated Castor Oil, PEG-80 Hydrogenated Castor Oil, PEG-100 Hydrogenated Castor Oil, PEG-200 Hydrogenated Castor Oil, PEG-30 Hydrogenated Lanolin, PEG-70 Hydrogenated Lanolin, PEG-50 Hydrogenated Palmamide, PEG-2 Isostearate, PEG-3 Isostearate, PEG-4 Isostearate, PEG-6 Isostearate, PEG-8 Isostearate, PEG-10 Isostearate, PEG-12 Isostearate, PEG-20 Isostearate, PEG-30 Isostearate, PEG-40 Isostearate, PEG-26 Jojoba Acid, PEG-40 Jojoba Acid, PEG-15 Jojoba Alcohol, PEG-26 Jojoba Alcohol, PEG-40 Jojoba Alcohol, PEG-35 Lanolin, PEG-40 Lanolin, PEG-50 Lanolin, PEG-55 Lanolin, PEG-60 Lanolin, PEG-70 Lanolin, PEG-75 Lanolin, PEG-85 Lanolin, PEG-100 Lanolin, PEG-150 Lanolin, PEG-75 Lanolin Oil, PEG-2 Lauramide, PEG-3 Lauramine Oxide, PEG-20 Laurate, PEG-32 Laurate, PEG-75 Laurate, PEG-150 Laurate, PEG-70 Mango Glycerides, PEG-20 Mannitan Laurate, PEG-8 Methyl Ether Dimethicone, PEG-120 Methyl Glucose Dioleate, PEG-80 Methyl Glucose Laurate, PEG-120 Methyl Glucose Trioleate, PEG-4 Montanate, PEG-30 Oleamine, PEG-20 Oleate, PEG-23 Oleate, PEG-32 Oleate, PEG-36 Oleate, PEG-75 Oleate, PEG-150 Oleate, PEG-20 Palmitate, PEG-150 Polyglyceryl-2 Tristearate, PEG/PPG-28/21 Acetate Dimethicone, PEG/PPG-24/18 Butyl Ether Dimethicone, PEG/PPG-3/17 Copolymer, PEG/PPG-5/35 Copolymer, PEG/PPG-8/55 Copolymer, PEG/PPG-10/30 Copolymer, PEG/PPG-10/65 Copolymer, PEG/PPG-12/35 Copolymer, PEG/PPG-16/17 Copolymer, PEG/PPG-20/9 Copolymer, PEG/PPG-20/20 Copolymer, PEG/PPG-20/60 Copolymer, PEG/PPG-20/65 Copolymer, PEG/PPG-22/25 Copolymer, PEG/PPG-28/30 Copolymer, PEG/PPG-30-35 Copolymer, PEG/PPG-30/55 Copolymer, PEG/PPG-35/40 Copolymer, PEG/PPG-50/40 Copolymer, PEG/PPG-150/35 Copolymer, PEG/PPG-160/30 Copolymer, PEG/PPG-190/60 Copolymer, PEG/PPG-200/40 Copolymer, PEG/PPG-300/55 Copolymer, PEG/PPG-20/22 Methyl Ether Dimethicone, PEG-26-PPG-30 Phosphate, PEG/PPG-4/2 Propylheptyl Ether, PEG/PPG-6/2 Propylheptyl Ether, PEG-7/PPG-2 Propylheptyl Ether, PEG/PPG-8/2 Propylheptyl Ether, PEG/PPG-10/2 Propylheptyl Ether, PEG/PPG-14/2 Propylheptyl Ether, PEG/PPG-40/2 Propylheptyl Ether, PEG/PPG-10/2 Ricinoleate, PEG/PPG-32/3 Ricinoleate, PEG-55 Propylene Glycol Oleate, PEG-25 Propylene Glycol Stearate, PEG-75 Propylene Glycol Stearate, PEG-120 Propylene Glycol Stearate, PEG-5 Rapeseed Sterol, PEG-10 Rapeseed Sterol, PEG-40 Ricinoleamide, PEG-75 Shea Butter Glycerides, PEG-75 Shorea Butter Glycerides, PEG-20 Sorbitan Cocoate, PEG-20 Sorbitan Isostearate, PEG-40 Sorbitan Lanolate, PEG-75 Sorbitan Lanolate, PEG-10 Sorbitan Laurate, PEG-40 Sorbitan Laurate, PEG-44 Sorbitan Laurate, PEG-75 Sorbitan Laurate, PEG-80 Sorbitan Laurate, PEG-20 Sorbitan Oleate, PEG-80 Sorbitan Palmitate, PEG-40 Sorbitan Stearate, PEG-60 Sorbitan Stearate, PEG-160 Sorbitan Triisostearate, PEG-40 Soy Sterol, PEG-2 Stearamide Carboxylic Acid, PEG-9 Stearamide Carboxylic Acid, PEG-20 Stearate, PEG-23 Stearate, PEG-25 Stearate, PEG-30 Stearate, PEG-32 Stearate, PEG-35 Stearate, PEG-36 Stearate, PEG-40 Stearate, PEG-45 Stearate, PEG-50 Stearate, PEG-55 Stearate, PEG-75 Stearate, PEG-90 Stearate, PEG-100 Stearate, PEG-120 Stearate, PEG-150 Stearate, PEG-45 Stearate Phosphate, PEG-20 Tallate, PEG-50 Tallow Amide, PEG-2 Tallowamide DEA, PEG-20 Tallowate, PEG-66 Trihydroxystearin, PEG-200 Trihydroxystearin, PEG-60 Tsubakiate Glycerides, Pelargonic Acid, Pentadoxynol-200, Pheneth-6 Phosphate, Poloxamer 105, Poloxamer 108, Poloxamer 182, Poloxamer 183, Poloxamer 184, Poloxamer 188, Poloxamer 217, Poloxamer 234, Poloxamer 235, Poloxamer 237, Poloxamer 238, Poloxamer 288, Poloxamer 334, Poloxamer 335, Poloxamer 338, Poloxamine 908, Poloxamine 1508, Polydimethylsiloxy PEG/PPG-24/19 Butyl Ether Silsesquioxane, Polydimethylsiloxy PPG-13 Butyl Ether Silsesquioxane, Polyglyceryl-6 Caprate, Polyglyceryl-10 Dilaurate, Polyglyceryl-20 Heptacaprylate, Polyglyceryl-20 Hexacaprylate, Polyglyceryl-2 Lauryl Ether, Polyglyceryl-10 Lauryl Ether, Polyglyceryl-20 Octaisononanoate, Polyglyceryl-6 Pentacaprylate, Polyglyceryl-10 Pentacaprylate, Polyglyceryl-3 Polydimethylsiloxyethyl Dimethicone, Polyglyceryl-6 Tetracaprylate, Polyglyceryl-10 Tetralaurate, Polyglyceryl-6 Tricaprylate, Polyglyceryl-10 Trilaurate, Polyquaternium-77, Polyquaternium-78, Polyquaternium-79, Polyquaternium-80, Polyquaternium-81, Polyquaternium-82, Pomaderris Kumerahou Flower/Leaf Extract, Poria Cocos Extract, Potassium Abietoyl Hydrolyzed Collagen, Potassium Babassuate, Potassium Behenate, Potassium C9-15 Alkyl Phosphate, Potassium C11-15 Alkyl Phosphate, Potassium C12-13 Alkyl Phosphate, Potassium C12-14 Alkyl Phosphate, Potassium Caprate, Potassium Capryloyl Glutamate, Potassium Capryloyl Hydrolyzed Rice Protein, Potassium Castorate, Potassium Cocoate, Potassium Cocoyl Glutamate, Potassium Cocoyl Glycinate, Potassium Cocoyl Hydrolyzed Casein, Potassium Cocoyl Hydrolyzed Collagen, Potassium Cocoyl Hydrolyzed Corn Protein, Potassium Cocoyl Hydrolyzed Keratin, Potassium Cocoyl Hydrolyzed Oat Protein, Potassium Cocoyl Hydrolyzed Potato Protein, Potassium Cocoyl Hydrolyzed Rice Bran Protein, Potassium Cocoyl Hydrolyzed Rice Protein, Potassium Cocoyl Hydrolyzed Silk, Potassium Cocoyl Hydrolyzed Soy Protein, Potassium Cocoyl Hydrolyzed Wheat Protein, Potassium Cocoyl Hydrolyzed Yeast Protein, Potassium Cocoyl PCA, Potassium Cocoyl Sarcosinate, Potassium Cocoyl Taurate, Potassium Cornate, Potassium Cyclocarboxypropyloleate, Potassium Dihydroxyethyl Cocamine Oxide Phosphate, Potassium Dimethicone PEG-7 Phosphate, Potassium Dodecylbenzenesulfonate, Potassium Hempseedate, Potassium Hydrogenated Cocoate, Potassium Hydrogenated Palmate, Potassium Hydrogenated Tallowate, Potassium Hydroxystearate, Potassium Isostearate, Potassium Lanolate, Potassium Laurate, Potassium Laureth-3 Carboxylate, Potassium Laureth-4 Carboxylate, Potassium Laureth-5 Carboxylate, Potassium Laureth-6 Carboxylate, Potassium Laureth-10 Carboxylate, Potassium Laureth Phosphate, Potassium Lauroyl Collagen Amino Acids, Potassium Lauroyl Glutamate, Potassium Lauroyl Hydrolyzed Collagen, Potassium Lauroyl Hydrolyzed Pea Protein, Potassium Lauroyl Hydrolyzed Soy Protein, Potassium Lauroyl PCA, Potassium Lauroyl Pea Amino Acids, Potassium Lauroyl Sarcosinate, Potassium Lauroyl Silk Amino Acids, Potassium Lauroyl Wheat Amino Acids, Potassium Lauryl Phosphate, Potassium Lauryl Sulfate, Potassium Linoleate, Potassium Metaphosphate, Potassium Methyl Cocoyl Taurate, Potassium Myristate, Potassium Myristoyl Glutamate, Potassium Myristoyl Hydrolyzed Collagen, Potassium Octoxynol-12 Phosphate, Potassium Oleate, Potassium Oleoyl Hydrolyzed Collagen, Potassium Olivate, Potassium Olivoyl Hydrolyzed Oat Protein, Potassium Olivoyl Hydrolyzed Wheat Protein, Potassium Olivoyl/Lauroyl Wheat Amino Acids, Potassium Olivoyl PCA, Potassium Palmate, Potassium Palmitate, Potassium Palmitoyl Hydrolyzed Corn Protein, Potassium Palmitoyl Hydrolyzed Oat Protein, Potassium Palmitoyl Hydrolyzed Rice Protein, Potassium Palmitoyl Hydrolyzed Sweet Almond Protein, Potassium Palmitoyl Hydrolyzed Wheat Protein, Potassium Palm Kernelate, Potassium Peanutate, Potassium Rapeseedate, Potassium Ricinoleate, Potassium Safflowerate, Potassium Soyate, Potassium Stearate, Potassium Stearoyl Hydrolyzed Collagen, Potassium Tallate, Potassium Tallowate, Potassium Taurate, Potassium Taurine Laurate, Potassium Trideceth-3 Carboxylate, Potassium Trideceth-4 Carboxylate, Potassium Trideceth-7 Carboxylate, Potassium Trideceth-15 Carboxylate, Potassium Trideceth-19 Carboxylate, Potassium Trideceth-6 Phosphate, Potassium Trideceth-7 Phosphate, Potassium Tsubakiate, Potassium Undecylenate, Potassium Undecylenoyl Hydrolyzed Collagen, Potassium Undecylenoyl Hydrolyzed Rice Protein, PPG-30-Buteth-30, PPG-36-Buteth-36, PPG-38-Buteth-37, PPG-30-Capryleth-4 Phosphate, PPG-10 Cetyl Ether Phosphate, PPG-2 C9-11 Pareth-8, PPG-1-Deceth-5, PPG-3-Deceth-2 Carboxylic Acid, PPG-30 Ethylhexeth-4 Phosphate, PPG-20-Glycereth-30, PPG-2 Hydroxyethyl Coco/Isostearamide, PPG-2-lsodeceth-8, PPG-2-lsodeceth-10, PPG-2-lsodeceth-18, PPG-2-lsodeceth-25, PPG-4-lsodeceth-10, Propyltrimonium Hydrolyzed Collagen, Quaternium-24, Quaternium-52, Quaternium-87, Rapeseed Acid, Rice Bran Acid, Rice Oil Glycereth-8 Esters, Ricinoleamidopropyl Betaine, Ricinoleic Acid, Ricinoleth-40, Safflower Acid, Sapindus Oahuensis Fruit Extract, Saponaria Officinalis Root Powder, Saponins, Sekken-K, Sekken-Na/K, Sekken Soji, Sekken Soji-K, Sesame Oil Glycereth-8 Esters, Sesamidopropylamine Oxide, Sesamidopropyl Betaine, Shea Butteramidopropyl Betaine, Shea Butter Glycereth-8 Esters, Sodium Arachidate, Sodium Arganampohoacetate, Sodium Astrocaryum Murumuruate, Sodium Avocadoate, Sodium Babassuamphoacetate, Sodium Babassuate, Sodium Babassu Sulfate, Sodium Behenate, Sodium Bisglycol Ricinosulfosuccinate, Sodium Bis-Hydroxyethylglycinate Coco-Glucosides Crosspolymer, Sodium Bis-Hydroxyethylglycinate Lauryl-Glucosides Crosspolymer, Sodium Borageamidopropyl PG-Dimonium Chloride Phosphate, Sodium Butoxynol-12 Sulfate, Sodium Butylglucosides Hydroxypropyl Phosphate, Sodium C13-17 Alkane Sulfonate, Sodium C14-18 Alkane Sulfonate, Sodium C12-15 Alkoxypropyl Iminodipropionate, Sodium C10-16 Alkyl Sulfate, Sodium C11-15 Alkyl Sulfate, Sodium C12-13 Alkyl Sulfate, Sodium C12-15 Alkyl Sulfate, Sodium C12-18 Alkyl Sulfate, Sodium C16-20 Alkyl Sulfate, Sodium C9-22 Alkyl Sec Sulfonate, Sodium C14-17 Alkyl Sec Sulfonate, Sodium Caprate, Sodium Caproamphoacetate, Sodium Caproamphohydroxypropylsulfonate, Sodium Caproamphopropionate, Sodium Caproyl Methyltaurate, Sodium Caprylate, Sodium Capryleth-2 Carboxylate, Sodium Capryleth-9 Carboxylate, Sodium Capryloamphoacetate, Sodium Capryloamphohydroxypropylsulfonate, Sodium Capryloamphopropionate, Sodium Capryloyl Glutamate, Sodium Capryloyl Hydrolyzed Wheat Protein, Sodium Caprylyl PG-Sulfonate, Sodium Caprylyl Sulfonate, Sodium Castorate, Sodium Ceteareth-13 Carboxylate, Sodium Cetearyl Sulfate, Sodium Ceteth-13 Carboxylate, Sodium Cetyl Sulfate, Sodium Cocamidopropyl PG-Dimonium Chloride Phosphate, Sodium Cocaminopropionate, Sodium Coceth Sulfate, Sodium Coceth-30 Sulfate, Sodium Cocoabutteramphoacetate, Sodium Cocoa Butterate, Sodium Cocoamphoacetate, Sodium Cocoamphohydroxypropylsulfonate, Sodium Cocoamphopropionate, Sodium Cocoate, Sodium Coco/Babassu/Andiroba Sulfate, Sodium Coco/Babassu Sulfate, Sodium Cocoglucosides Hydroxypropyl Phosphate, Sodium Cocoglucosides Hydroxypropylsulfonate, Sodium CocoGlucoside Tartrate, Sodium Cocoglyceryl Ether Sulfonate, Sodium Coco/Hydrogenated Tallow Sulfate, Sodium Cocoiminodiacetate, Sodium Cocomonoglyceride Sulfate, Sodium Cocomonoglyceride Sulfonate, Sodium Coco PG-Dimonium Chloride Phosphate, Sodium CocoSulfate, Sodium Coco Sulfoacetate, Sodium Cocoyl Alaninate, Sodium Cocoyl Amino Acids, Sodium Cocoyl Collagen Amino Acids, Sodium Cocoyl Glutamate, Sodium Cocoyl Glutaminate, Sodium Cocoyl Glycinate, Sodium Cocoyl/Hydrogenated Tallow Glutamate, Sodium Cocoyl Hydrolyzed Collagen, Sodium Cocoyl Hydrolyzed Keratin, Sodium Cocoyl Hydrolyzed Rice Protein, Sodium Cocoyl Hydrolyzed Silk, Sodium Cocoyl Hydrolyzed Soy Protein, Sodium Cocoyl Hydrolyzed Sweet Almond Protein, Sodium Cocoyl Hydrolyzed Wheat Protein, Sodium Cocoyl Hydrolyzed Wheat Protein Glutamate, Sodium Cocoyl Isethionate, Sodium Cocoyl Methylaminopropionate, Sodium Cocoyl Oat Amino Acids, Sodium Cocoyl/Palmoyl/Sunfloweroyl Glutamate, Sodium Cocoyl Proline, Sodium Cocoyl Sarcosinate, Sodium Cocoyl Taurate, Sodium Cocoyl Threoninate, Sodium Cocoyl Wheat Amino Acids, Sodium C12-14 Olefin Sulfonate, Sodium C14-16 Olefin Sulfonate, Sodium C14-18 Olefin Sulfonate, Sodium C16-18 Olefin Sulfonate, Sodium Cornamphopropionate, Sodium Cotton-seed-amphoacetate, Sodium C13-15 Pareth-8 Butyl Phosphate, Sodium C9-11 Pareth-6 Carboxylate, Sodium C11-15 Pareth-7 Carboxylate, Sodium C12-13 Pareth-5 Carboxylate, Sodium C12-13 Pareth-8 Carboxylate, Sodium C12-13 Pareth-12 Carboxylate, Sodium C12-15 Pareth-6 Carboxylate, Sodium C12-15 Pareth-7 Carboxylate, Sodium C12-15 Pareth-8 Carboxylate, Sodium C14-15 Pareth-8 Carboxylate, Sodium C12-14 Sec-Pareth-8 Carboxylate, Sodium C14-15 Pareth-PG Sulfonate, Sodium C12-13 Pareth-2 Phosphate, Sodium C13-15 Pareth-8 Phosphate, Sodium C9-15 Pareth-3 Sulfate, Sodium C10-15 Pareth Sulfate, Sodium C10-16 Pareth-2 Sulfate, Sodium C12-13 Pareth Sulfate, Sodium C12-15 Pareth Sulfate, Sodium C12-15 Pareth-3 Sulfate, Sodium C13-15 Pareth-3 Sulfate, Sodium C12-14 Sec-Pareth-3 Sulfate, Sodium C12-15 Pareth-3 Sulfonate, Sodium C12-15 Pareth-7 Sulfonate, Sodium C12-15 Pareth-15 Sulfonate, Sodium Deceth-2 Carboxylate, Sodium Deceth Sulfate, Sodium Decylbenzenesulfonate, Sodium Decylglucosides Hydroxypropyl Phosphate, Sodium Decyl-glucosides Hydroxypropylsulfonate, Sodium Dilaureth-7 Citrate, Sodium Dilaureth-10 Phosphate, Sodium Dilinoleamidopropyl PG-Dimonium Chloride Phosphate, Sodium Dilinoleate, Sodium Dioleth-8 Phosphate, Sodium Dodecylbenzenesulfonate, Sodium Ethyl 2-Sulfolaurate, Sodium Glyceryl Oleate Phosphate, Sodium Grapeseedamidopropyl PG-Dimonium Chloride Phosphate, Sodium Grapeseedamphoacetate, Sodium Grapeseedate, Sodium Hempseedamphoacetate, Sodium Hexeth-4 Carboxylate, Sodium Hydrogenated Cocoate, Sodium Hydrogenated Cocoyl Methyl Isethionate, Sodium Hydrogenated Palmate, Sodium Hydrogenated Tallowate, Sodium Hydrogenated Tallowoyl Glutamate, Sodium Hydroxylauryldimonium Ethyl Phosphate, Sodium Hydroxypropyl Palm Kernelate Sulfonate, Sodium Hydroxypropylphosphate Decylglucoside Crosspolymer, Sodium Hydroxypropylphosphate Laurylglucoside Crosspolymer, Sodium Hydroxypropylsulfonate Cocoglucoside Crosspolymer, Sodium Hydroxypropylsulfonate Decylglucoside Crosspolymer, Sodium Hydroxypropylsulfonate Laurylglucoside Crosspolymer, Sodium Hydroxystearate, Sodium Isostearate, Sodium lsosteareth-6 Carboxylate, Sodium Isosteareth-11 Carboxylate, Sodium Isostearoamphoacetate, Sodium Isostearoamphopropionate, Sodium N-Isostearoyl Methyltaurate, Sodium Laneth Sulfate, Sodium Lanolate, Sodium Lardate, Sodium Lauramido Diacetate, Sodium Lauraminopropionate, Sodium Laurate, Sodium Laureth-3 Carboxylate, Sodium Laureth-4 Carboxylate, Sodium Laureth-5 Carboxylate, Sodium Laureth-6 Carboxylate, Sodium Laureth-8 Carboxylate, Sodium Laureth-11 Carboxylate, Sodium Laureth-12 Carboxylate, Sodium Laureth-13 Carboxylate, Sodium Laureth-14 Carboxylate, Sodium Laureth-16 Carboxylate, Sodium Laureth-17 Carboxylate, Sodium Laureth Sulfate, Sodium Laureth-5 Sulfate, Sodium Laureth-7 Sulfate, Sodium Laureth-8 Sulfate, Sodium Laureth-12 Sulfate, Sodium Laureth-40 Sulfate, Sodium Laureth-7 Tartrate, Sodium Lauriminodipropionate, Sodium Lauroamphoacetate, Sodium Lauroamphohydroxypropylsulfonate, Sodium Lauroampho PG-Acetate Phosphate, Sodium Lauroamphopropionate, Sodium Lauroyl Aspartate, Sodium Lauroyl Collagen Amino Acids, Sodium Lauroyl Glycine Propionate, Sodium Lauroyl Hydrolyzed Collagen, Sodium Lauroyl Hydrolyzed Silk, Sodium Lauroyl Hydroxypropyl Sulfonate, Sodium Lauroyl Isethionate, Sodium Lauroyl Methylaminopropionate, Sodium Lauroyl Methyl Isethionate, Sodium Lauroyl Millet Amino Acids, Sodium Lauroyl/Myristoyl Aspartate, Sodium Lauroyl Oat Amino Acids, Sodium Lauroyl Sarcosinate, Sodium Lauroyl Silk Amino Acids, Sodium Lauroyl Taurate, Sodium Lauroyl Wheat Amino Acids, Sodium Lauryl Diethylenediaminoglycinate, Sodium Lauryl Glucose Carboxylate, Sodium Laurylglucosides Hydroxypropyl Phosphate, Sodium Laurylglucosides Hydroxypropylsulfonate, Sodium Lauryl Glycol Carboxylate, Sodium Lauryl Hydroxyacetamide Sulfate, Sodium Lauryl Phosphate, Sodium Lauryl Sulfate, Sodium Lauryl Sulfoacetate, Sodium Linoleate, Sodium Macadamiaseedate, Sodium Mangoamphoacetate, Sodium Mangoseedate, Sodium/MEA Laureth-2 Sulfosuccinate, Sodium Methoxy PPG-2 Acetate, Sodium Methyl Cocoyl Taurate, Sodium Methyl Lauroyl Taurate, Sodium Methyl Myristoyl Taurate, Sodium Methyl Oleoyl Taurate, Sodium Methyl Palmitoyl Taurate, Sodium Methyl Stearoyl Taurate, Sodium Methyl 2-Sulfolaurate, Sodium Methyl 2-Sulfopalmitate, Sodium Methyltaurate Isopalmitamide, Sodium Methyltaurine Cocoyl Methyltaurate, Sodium Myreth Sulfate, Sodium Myristate, Sodium Myristoamphoacetate, Sodium Myristoyl Glutamate, Sodium Myristoyl Hydrolyzed Collagen, Sodium Myristoyl Isethionate, Sodium Myristoyl Sarcosinate, Sodium Myristyl Sulfate, Sodium Nonoxynol-6 Phosphate, Sodium Nonoxynol-9 Phosphate, Sodium Nonoxynol-1 Sulfate, Sodium Nonoxynol-3 Sulfate, Sodium Nonoxynol-4 Sulfate, Sodium Nonoxynol-6 Sulfate, Sodium Nonoxynol-8 Sulfate, Sodium Nonoxynol-10 Sulfate, Sodium Nonoxynol-25 Sulfate, Sodium Octoxynol-2 Ethane Sulfonate, Sodium Octoxynol-2 Sulfate, Sodium Octoxynol-6 Sulfate, Sodium Octoxynol-9 Sulfate, Sodium Oleate, Sodium Oleoamphoacetate, Sodium Oleoamphohydroxypropylsulfonate, Sodium Oleoamphopropionate, Sodium Oleoyl Hydrolyzed Collagen, Sodium Oleoyl Isethionate, Sodium Oleth Sulfate, Sodium Oleyl Methyl Isethionate, Sodium Oleyl Sulfate, Sodium Olivamphoacetate, Sodium Olivate, Sodium Olivoyl Glutamate, Sodium Palmamphoacetate, Sodium Palmate, Sodium Palm Glyceride Sulfonate, Sodium Palmitate, Sodium Palmitoyl Hydrolyzed Collagen, Sodium Palmitoyl Hydrolyzed Wheat Protein, Sodium Palmitoyl Sarcosinate, Sodium Palm Kernelate, Sodium Palm Kerneloyl Isethionate, Sodium Palmoyl Glutamate, Sodium Passiflora Edulis Seedate, Sodium Peanutamphoacetate, Sodium Peanutate, Sodium PEG-6 Cocamide Carboxylate, Sodium PEG-8 Cocamide Carboxylate, Sodium PEG-4 Cocamide Sulfate, Sodium PEG-3 Lauramide Carboxylate, Sodium PEG-4 Lauramide Carboxylate, Sodium PEG-8 Palm Glycerides Carboxylate, Sodium Pentaerythrityl Hydroxypropyl Iminodiacetate Dendrimer, Sodium Propoxy PPG-2 Acetate, Sodium Rapeseedate, Sodium Ricebranamphoacetate, Sodium Ricinoleate, Sodium Ricinoleoamphoacetate, Sodium Rose Hipsamphoacetate, Sodium Rosinate, Sodium Safflowerate, Sodium Saffloweroyl Hydrolyzed Soy Protein, Sodium Sesameseedate, Sodium Sesamphoacetate, Sodium Sheabutteramphoacetate, Sodium Soyate, Sodium Soy Hydrolyzed Collagen, Sodium Stearate, Sodium Stearoamphoacetate, Sodium Stearoamphohydroxypropylsulfonate, Sodium Stearoamphopropionate, Sodium Stearoyl Casein, Sodium Stearoyl Glutamate, Sodium Stearoyl Hyaluronate, Sodium Stearoyl Hydrolyzed Collagen, Sodium Stearoyl Hydrolyzed Corn Protein, Sodium Stearoyl Hydrolyzed Silk, Sodium Stearoyl Hydrolyzed Soy Protein, Sodium Stearoyl Hydrolyzed Wheat Protein, Sodium Stearoyl Lactalbumin, Sodium Stearoyl Methyl Isethionate, Sodium Stearoyl Oat Protein, Sodium Stearoyl Pea Protein, Sodium Stearoyl Soy Protein, Sodium Stearyl Dimethyl Glycine, Sodium Stearyl Sulfate, Sodium Sunflowerseedamphoacetate, Sodium Surfactin, Sodium Sweetalmondamphoacetate, Sodium Sweet Almondate, Sodium Tallamphopropionate, Sodium Tallate, Sodium Tallowamphoacetate, Sodium Tallowate, Sodium Tallow Sulfate, Sodium Tamanuseedate, Sodium Taurate, Sodium Taurine Cocoyl Methyltaurate, Sodium Taurine Laurate, Sodium/TEA-Lauroyl Collagen Amino Acids, Sodium/TEA-Lauroyl Hydrolyzed Collagen, Sodium/TEA-Lauroyl Hydrolyzed Keratin, Sodium/TEA-Lauroyl Keratin Amino Acids, Sodium/TEA-Undecylenoyl Collagen Amino Acids, Sodium/TEA-Undecylenoyl Hydrolyzed Collagen, Sodium/TEA-Undecylenoyl Hydrolyzed Corn Protein, Sodium/TEA-Undecylenoyl Hydrolyzed Soy Protein, Sodium/TEA-Undecylenoyl Hydrolyzed Wheat Protein, Sodium Theobroma Grandiflorum Seedate, Sodium Trideceth-3 Carboxylate, Sodium Trideceth-4 Carboxylate, Sodium Trideceth-6 Carboxylate, Sodium Trideceth-7 Carboxylate, Sodium Trideceth-8 Carboxylate, Sodium Trideceth-12 Carboxylate, Sodium Trideceth-15 Carboxylate, Sodium Trideceth-19 Carboxylate, Sodium Trideceth Sulfate, Sodium Tridecylbenzenesulfonate, Sodium Tridecyl Sulfate, Sodium Trimethylolpropane Hydroxypropyl Iminodiacetate Dendrimer, Sodium Undeceth-5 Carboxylate, Sodium Undecylenate, Sodium Undecylenoamphoacetate, Sodium Undecylenoamphopropionate, Sodium Undecylenoyl Glutamate, Sodium Wheat Germamphoacetate, Sorbeth-160 Tristearate, Soy Acid, Soyamidopropylamine Oxide, Soyamidopropyl Betaine, Soybean Oil Glycereth-8 Esters, Stearamidopropylamine Oxide, Stearamidopropyl Betaine, Stearamine Oxide, Steareth-15, Steareth-16, Steareth-20, Steareth-21, Steareth-25, Steareth-27, Steareth-30, Steareth-40, Steareth-50, Steareth-80, Steareth-100, Steareth-2 Phosphate, Steareth-3 Phosphate, Stearic Acid, Stearoxypropyltrimonium Chloride, Stearoyl Glutamic Acid, Stearoyl Sarcosine, Stearyl Betaine, Stearyldimoniumhydroxypropyl Butylglucosides Chloride, Stearyldimoniumhydroxypropyl Decylglucosides Chloride, Stearyldimoniumhydroxypropyl Laurylglucosides Chloride, Sulfated Castor Oil, Sulfated Coconut Oil, Sulfated Glyceryl Oleate, Sulfated Olive Oil, Sulfated Peanut Oil, Sunfloweramide MEA, Sunflower Seed Acid, Sunflowerseedamidopropyl Hydroxyethyldimonium Chloride, Sunflower Seed Oil Glycereth-8 Esters, Tall Oil Acid, Tallow Acid, Tallowamidopropylamine Oxide, Tallowamidopropyl Betaine, Tallowamidopropyl Hydroxysultaine, Tallowamine Oxide, Tallow Betaine, Tallow Dihydroxyethyl Betaine, Tallowoyl Ethyl Glucoside, TEA-Abietoyl Hydrolyzed Collagen, TEA-C12-14 Alkyl Phosphate, TEA-C10-15 Alkyl Sulfate, TEA-C11-15 Alkyl Sulfate, TEA-C12-13 Alkyl Sulfate, TEA-C12-14 Alkyl Sulfate, TEA-C12-15 Alkyl Sulfate, TEA C14-17 Alkyl Sec Sulfonate, TEA-Canolate, TEA-Cocamide Diacetate, TEA-Cocoate, TEA-Coco-Sulfate, TEA-Cocoyl Alaninate, TEA-Cocoyl Glutamate, TEA-Cocoyl Glutaminate, TEA-Cocoyl Glycinate, TEA-Cocoyl Hydrolyzed Collagen, TEA-Cocoyl Hydrolyzed Soy Protein, TEA-Cocoyl Sarcosinate, TEA- Dimethicone PEG-7 Phosphate, TEA-Dodecylbenzenesulfonate, TEA-Hydrogenated Cocoate, TEA-Hydrogenated Tallowoyl Glutamate, TEA-Isostearate, TEA-Isostearoyl Hydrolyzed Collagen, TEA-Lauraminopropionate, TEA-Laurate, TEA-Laurate/Myristate, TEA-Laureth Sulfate, TEA-Lauroyl Collagen Amino Acids, TEA-Lauroyl Glutamate, TEA-Lauroyl Hydrolyzed Collagen, TEA-Lauroyl Keratin Amino Acids, TEA-Lauroyl Methylaminopropionate, TEA-Lauroyl/Myristoyl Aspartate, TEA-Lauroyl Sarcosinate, TEA-Lauryl Phosphate, TEA-Lauryl Sulfate, TEA-Myristaminopropionate, TEA-Myristate, TEA-Myristoyl Hydrolyzed Collagen, TEA-Oleate, TEA-Oleoyl Hydrolyzed Collagen, TEA-Oleoyl Sarcosinate, TEA-Oleyl Sulfate, TEA-Palmitate, TEA-Palm Kernel Sarcosinate, TEA-PEG-3 Cocamide Sulfate, TEA-Rosinate, TEA-Stearate, TEA-Tallate, TEA-T ridecylbenzenesulfonate, TEA-Undecylenate, TEA-Undecylenoyl Hydrolyzed Collagen, Tetramethyl Decynediol, Tetrasodium Dicarboxyethyl Stearyl Sulfosuccinamate, TIPA-Laureth Sulfate, TI PA-Lauryl Sulfate, TIPA-Myristate, TIPA-Stearate, Tocopheryl Phosphate, Trehalose Undecylenoate, TM-C12-15 Pareth-2 Phosphate, TM-C12-15 Pareth-6 Phosphate, TM-C12-15 Pareth-8 Phosphate, TM-C12-15 Pareth-10 Phosphate, Trideceth-20, Trideceth-50, Trideceth-3 Carboxylic Acid, Trideceth-4 Carboxylic Acid, Trideceth-7 Carboxylic Acid, Trideceth-8 Carboxylic Acid, Trideceth-15 Carboxylic Acid, Trideceth-19 Carboxylic Acid, Trideceth-10 Phosphate, Tridecylbenzenesulfonic Acid, Trilaureth-9 Citrate, Trimethylolpropane Hydroxypropyl Bis-Hydroxyethylamine Dendrimer, Trisodium Lauroampho PG-Acetate Chloride Phosphate, Undecanoic Acid, Undeceth-5 Carboxylic Acid, Undecylenamidopropylamine Oxide, Undecylenamidopropyl Betaine, Undecylenic Acid, Undecylenoyl Collagen Amino Acids, Undecylenoyl Glycine, Undecylenoyl Hydrolyzed Collagen, Undecylenoyl Wheat Amino Acids, Undecyl Glucoside, Wheat Germ Acid, Wheat Germamidopropylamine Oxide, Wheat Germamidopropyl Betaine, Yucca Schidigera Leaf/Root/Stem Extract, Yucca Schidigera Stem Extract, Zinc Coceth Sulfatea and Zinc Coco-Sulfate.

Preferred are one or more compounds selected from the group consisting of Sodium Laureth Sulfate, Cocamidopropyl Betaine, Sodium Cocoamphoacetate, CocoGlucoside and Ammonium Lauryl Sulfosuccinate.

The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other non-ionic or cationic surfactants may also be added to the preparations as emulsifiers, including for example:
  products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
  $C_{12/18}$ fatty acid monoesters and diesters of addition products of 1 to 30 mol ethylene oxide onto glycerol;
  glycerol mono- and diesters and sorbitan mono- and diesters of saturated and unsaturated fatty acids containing 6 to 22 carbon atoms and ethylene oxide addition products thereof;
  addition products of 15 to 60 mol ethylene oxide onto castor oil and/or hydrogenated castor oil;
  polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
  addition products of 2 to 15 mol ethylene oxide onto castor oil and/or hydrogenated castor oil;
  partial esters based on linear, branched, unsaturated or saturated $C_{6/22}$ fatty acids, ricin-oleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);
  mono-, di and trialkyl phosphates and mono-, di- and/or tri-PEG-alkyl phosphates and salts thereof;
  wool wax alcohols;
  polysiloxane/polyalkyl polyether copolymers and corresponding derivatives;
  mixed esters of pentaerythritol, fatty acids, citric acid and fatty alcohol and/or mixed esters of $C_{6-22}$ fatty acids, methyl glucose and polyols, preferably glycerol or polyglycerol, alkyl and/or alkenyloligoglycosides;
polyalkylene glycols and
glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Belling®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Alkyl and/or alkenyl oligoglycosides. Alkyl and/or alkenyl oligoglycosides, their preparation and their use are known from the prior art. They are prepared in particular by reacting glucose or oligosaccharides with primary alcohols containing 8 to 18 carbon atoms. With regard to the glycoside residue, monoglycosides, in which a cyclic sugar residue is glycosidically bonded to the fatty alcohol, as well as oligomeric glycosides with a degree of oligomerization up to preferably about 8 are suitable. The degree of oligomerization is a statistical mean value based on a homolog distribution customary for such technical products.

Tetraalkyl ammonium salts. Cationically active surfactants comprise the hydrophobic high molecular group required for the surface activity in the cation by dissociation in aqueous solution. A group of important representatives of the cationic surfactants are the tetraalkyl ammonium salts of the general formula: $(R^1R^2R^3R^4N^+)\ X^-$. Here R1 stands for $C_1$-$C_8$ alk(en)yl, $R^2$, $R^3$ and $R^4$, independently of each other, for alk(en)yl radicals having 1 to 22 carbon atoms. X is a counter ion, preferably selected from the group of the halides, alkyl sulfates and alkyl carbonates. Cationic surfactants, in which the nitrogen group is substituted with two long acyl groups and two short alk(en)yl groups, are particularly preferred.

Esterquats. A further class of cationic surfactants particularly useful as co-surfactants for the present invention is represented by the so-called esterquats. Esterquats are generally understood to be quaternised fatty acid triethanolamine ester salts. These are known compounds which can be obtained by the relevant methods of preparative organic chemistry. Reference is made in this connection to International patent application WO 91/01295 A1, according to which triethanolamine is partly esterified with fatty acids in the presence of hypophosphorous acid, air is passed through the reaction mixture and the whole is then quaternised with dimethyl sulphate or ethylene oxide. In addition, German patent DE 4308794 C1 describes a process for the production of solid esterquats in which the quaternisation of triethanolamine esters is carried out in the presence of suitable dispersants, preferably fatty alcohols.

Typical examples of esterquats suitable for use in accordance with the invention are products of which the acyl component derives from monocarboxylic acids corresponding to formula RCOOH in which RCO is an acyl group containing 6 to 10 carbon atoms, and the amine component is triethanolamine (TEA). Examples of such monocarboxylic acids are caproic acid, caprylic acid, capric acid and technical mixtures thereof such as, for example, so-called head-fractionated fatty acid. Esterquats of which the acyl component derives from monocarboxylic acids containing 8 to 10 carbon atoms, are preferably used. Other esterquats are those of which the acyl component derives from dicarboxylic acids like malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component derives from mixtures of monocarboxylic acids containing 6 to 22 carbon atoms, and adipic acid are preferably used. The molar ratio of mono and dicarboxylic acids in the final esterquat may be in the range from 1:99 to 99:1 and is preferably in the range from 50:50 to 90:10 and more particularly in the range from 70:30 to 80:20. Besides the quaternised fatty acid triethanolamine ester salts, other suitable esterquats are quaternized ester salts of mono-/dicarboxylic acid mixtures with diethanolalkyamines or 1,2-dihydroxypropyl dialkylamines. The esterquats may be obtained both from fatty acids and from the corresponding triglycerides in admixture with the corresponding dicarboxylic acids. One such process, which is intended to be representative of the relevant prior art, is proposed in European patent EP 0750606 B1. To produce the quaternised esters, the mixtures of mono- and dicarboxylic acids and the triethanolamine—based on the available carboxyl functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grunau), quaternized wheat polypeptides, polyethyleneimine, cationic silicone polymers such as, for example, amodimethicone, copolymers of adipic acid and dimethylaminohy-droxypropyl diethylenetriamine (Cartaretine®, Sandoz), copolymers of acrylic acid with dimethyl diallyl ammonium chloride (Merquat® 550, Chemviron), polyaminopolyamides and cross-linked water-soluble polymers thereof, cationic chitin derivatives such as, for example, quaternized chitosan, optionally in microcrystalline distribution, condensation products of dihaloalkyls, for example dibromobutane, with bis-dialkylamines, for example bisdimethylamino-1,3-propane, cationic guar gum such as, for example, Jaguar®CBS, Jaguar®C-17, Jaguar®C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamido-propyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicones can be chosen from the group consisting of: Acefylline Methylsilanol Mannuronate, Acetylmethionyl Methylsilanol Elastinate Acrylates/Behenyl, Acrylate/Dimethicone Methacrylate Copolymer, Acrylates/Behenyl Methacrylate/Dimethicone Methacrylate Copolymer, Acrylates/Bis-Hydroxypropyl Dimethicone Crosspolymer, Acrylates/Dimethicone Copolymer, Acrylates/Dimethicone Methacrylate/Ethylhexyl Acrylate Copolymer, Acrylates/Dimethiconol Acrylate Copolymer, Acrylates/Ethylhexyl Acrylate/Dimethicone Methacrylate Copolymer, Acrylates/Octylacrylamide/Diphenyl Amodimethicone Copolymer, Acrylates/Polytrimethylsiloxymethacrylate Copolymer, Acrylates/Propyl Trimethicone Methacrylate Copolymer, Acrylates/Stearyl Acrylate/Dimethicone Methacrylate Copolymer, Acrylates/Tridecyl Acrylate/Triethoxysilylpropyl Methacrylate/Dimethicone Methacrylate Copolymer, Acrylates/Trifluoropropylmethacrylate/Polytrimethyl Siloxymethacrylate Copolymer, Amino Bispropyl Dimethicone, Aminoethylaminopropyl Dimethicone, Aminopropyl Dimethicone, Aminopropyl Phenyl Trimethicone, Aminopropyl Triethoxysilane, Ammonium Dimethicone PEG-7 Sulfate, Amodimethicone, Amodimethicone Hydroxystearate, Amodimethicone/Silsesquioxane Copolymer, Ascorbyl Carboxydecyl Trisiloxane, Ascorbyl Methylsilanol Pectinate, Behenoxy Dimethicone, Behentrimonium Dimethicone PEG-8 Phthalate, Behenyl Dimethicone, Bisamino PEG/PPG-41/3 Aminoethyl PG-Propyl Dimethicone, Bis-Aminopropyl/Ethoxy Aminopropyl Dimethicone, Bis(Butylbenzoate) Diaminotriazine Aminopropyltrisiloxane, Bis-Butyldimethicone Polyglyceryl-3, Bis-Butyloxyamodimethicone/PEG-60 Copolymer, Bis (C13-15 Alkoxy) Hydroxybutamidoamodi-methicone, Bis (C13-15 Alkoxy) PG-Amodimethicone, Bis-(C1-8 Alkyl Lauroyl Lysine Decylcarboxamide) Dimethicone, Bis-Cetyl Cetyl Dimethicone, Bis-Cetyl/PEG-8 Cetyl PEG-8 Dimethicone, Bis-Diphenylethyl Disiloxane, Bis-Ethyl Ethyl Methicone, Bis-Gluconamidoethylaminopropyl Dimethicone, Bis-Hydrogen Dimethicone, Bis-Hydroxyethoxypropyl Dimethicone Bis-Hydroxylauryl, Dimethicone/IPDI Copolymer, Bis-Hydroxy/Methoxy Amodimethicone, Bis-Hydroxypropyl Dimethicone Behenate, Bis-Hydroxypropyl Dimethicone/SMDI Copolymer, Bis-Isobutyl PEG-14/Amodimethicone Copolymer, Bis-Isobutyl PEG-15/Amodimethicone Copolymer, Bis-Isobutyl PEG/PPG-20/35/Amodimethicone Copolymer, Bis-Isobutyl PEG/PPG-10/7/Dimethicone Copolymer, Bis-Isobutyl PEG-24/PPG-7/Dimethicone Copolymer, Bis-PEG-1 Dimethicone, Bis-PEG-4 Dimethicone, Bis-PEG-8 Dimethicone, Bis-PEG-12 Dimethicone,Bis-PEG-20 Dimethicone, Bis-PEG-12 Dimethicone Beeswax, Bis-PEG-12 Dimethicone Candelillate, Bis-PEG-15 Dimethicone/IPDI Copolymer, Bis-PEG-15 Methyl Ether Dimethicone, Bis-PEG-18 Methyl Ether Dimethyl Silane, Bis-PEG/PPG-14/14 Dimethicone, Bis-PEG/PPG-15/5 Dimethicone, Bis-PEG/PPG-18/6 Dimethicone, Bis-PEG/PPG-20/20 Dimethicone, Bis-PEG/PPG-16/16 PEG/PPG-16/16 Dimethicone, Bis-PEG/PPG-20/5 PEG/PPG-20/5 Dimethicone, Bisphenylhexamethicone, Bis-Phenylpropyl Dimethicone, Bispolyethylene Dimethicone, Bis-(Polyglyceryl-3 Oxyphenylpropyl) Dimethicone, Bis-(Polyglyceryl-7 Oxyphenylpropyl) Dimethicone, Bis-PEG-15 Dimethicone/I PDI Copolymer, Bis(PPG-7 Undeceneth-21) Dimethicone, Bis-Stearyl Dimethicone, Bis-Trimethoxysilylethyl Tetramethyl-disiloxyethyl Dimethicone, Bis-Vinyldimethicone, Bis-Vinyl Dimethicone/Dimethicone Copolymer, Borage Seed Oil PEG-7 Dimethicone Esters, Butyl Acrylate/C6-14 Perfluoroalkylethyl Acrylate/Mercaptopropyl Dimethicone Copolymer, Butyl Acrylate/Hydroxypropyl Dimethicone Acrylate Copolymer, Butyl Dimethicone Acrylate/Cyclohexylmethacrylate/Ethylhexyl Acrylate Copolymer, Butyldimethicone Methacrylate/Methyl Methacrylate Crosspolymer, t-Butyl Dimethyl Silyl Grape Seed Extract, Butyl Polydimethylsiloxyl Ethylene/Propylene/Vinylnorbornene Copolymer, C6-8 Alkyl C3-6 Alkyl Glucoside Dimethicone, C20-24 Alkyl Dimethicone,C24-28 Alkyl Dimethicone, C26-28 Alkyl Dimethicone, C30-45 Alkyl Dimethicone, C30-60 Alkyl Dimethicone, C32 Alkyl Dimethicone, C30-45 Alkyl Dimethicone/Polycyclohexene Oxide Crosspolymer, C26-28 Alkyldimethylsilyl Polypropylsilsesquioxane, C30-45 Alkyldimethylsilyl Polypropylsilsesquioxane, C20-24 Alkyl Methicone, C24-28 Alkyl Methicone, C26-28 Alkyl Methicone, C30-45 Alkyl Methicone, C20-28 Alkyl Perfluorodecylethoxy Dimethicone, C26-54 Alkyl Tetradecyl Dimethicone, Capryl Dimethicone, Caprylyl Dimethicone Ethoxy Glucoside, Caprylyl Methicone, Caprylyl Trimethicone, Carboxydecyl Trisiloxane, Castor Oil Bis-Hydroxypropyl Dimethicone Esters Cerotyl Dimethicone, Cetearyl Dimethicone Crosspolymer, Cetearyl Dimethicone/Vinyl Dimethicone Crosspolymer, Cetearyl Methicone, Cetrimonium Carboxydecyl PEG-8 Dimethicone, Cetrimonium Dimethicone PEG-7 Phthalate, Cetyl Behenyl Dimethicone, Cetyl Dimethicone, Cetyl Dimethicone/Bis-Vinyldimethicone Crosspolymer, Cetyl Hexacosyl Dimethicone, Cetyloxy Dimethicone, Cetyl PEG-8 Dimethicone, Cetyl PEG/PPG-15/15 Butyl Ether Dimethicone, Cetyl PEG/PPG-7/3 Dimethicone, Cetyl PEG/PPG-10/1 Dimethicone, Cetyl Triethylmonium Dimethicone PEG-8 Phthalate, Cetyl Triethylmonium Dimethicone PEG-8 Succinate, Copper Acetyl Tyrosinate Methylsilanol, Copper PCA Methylsilanol, C4-14 Perfluoroalkylethoxy Dimethicone, Cycloethoxymethicone, Cycloheptasiloxane, Cyclohexasiloxane, Cyclomethicone, Cyclopentasiloxane, Cyclophenylmethicone, Cyclotetrasiloxane,mCyclovinylmethicone, Cystine Bis-PG-Propyl Silanetriol, DEA PG-Propyl PEG/PPG-18/21 Dimethicone, Diisostearoyl Trimethylolpropane Siloxy Silicate, Dilauroyl Trimethylolpropane Siloxy Silicate, Dilinoleamidopropyl Dimethylamine Dimethicone PEG-7 Phosphate, Dimethicone, Dimethicone Crosspolymer, Dimethicone Crosspolymer-3, Dimethicone/Divinyldimethicone/Silsesquioxane Crosspolymer, Dimethicone Ethoxy Glucoside, Dimethicone Hydroxypropyl Trimonium Chloride, Dimethicone/Mercaptopropyl Methicone Copolymer, Dimethicone PEG-15 Acetate Dimethicone PEG-8 Adipate, Dimethicone PEG-7 Avocadoate, Dimethicone PEG-8 Avocadoate, Dimethicone PEG-8 Beeswax, Dimethicone PEG-8 Benzoate, Dimethicone PEG-8 Borageate, Dimethicone PEG-7 Cocoate, Dimethicone/PEG-10 Crosspolymer, Dimethicone/PEG-10/15 Crosspolymer, Dimethicone/PEG-15 Crosspolymer, Dimethicone PEG-7 Isostearate, Dimethicone PEG-8 Isostearate, Dimethicone PEG-7 Lactate, Dimethicone PEG-8 Lanolate, Dimethicone PEG-8 Laurate, Dimethicone PEG-8 Meadowfoamate, Dimethicone PEG-7 Octyldodecyl Citrate, Dimethicone PEG-7 Olivate, Dimethicone PEG-8 Olivate, Dimethicone PEG-7 Phosphate, Dimethicone PEG-8 Phosphate, Dimethicone PEG-10 Phosphate, Dimethicone PEG-7 Phthalate, Dimethicone PEG-8 Phthalate, Dimethicone PEG-8 Polyacrylate, Dimethicone PEG/PPG-20/23 Benzoate, Dimethicone PEG/PPG-7/4 Phosphate, Dimethicone PEG/PPG-12/4 Phosphate, Dimethicone PEG-7 Succinate, Dimethicone PEG-8 Succinate, Dimethicone PEG-7 Sulfate, Dimethicone PEG-7 Undecylenate, Dimethicone PG-Diethylmonium Chloride, Dimethicone/Phenyl Vinyl Dimethicone Crosspolymer, Dimethicone/Polyglycerin-3 Crosspolymer, Dimethicone/PPG-20 Crosspolymer, Dimethicone Propylethylenediamine Behenate, Dimethicone Propyl PG-Betaine, Dimethicone/Silsesquioxane Copolymer, Dimethicone Silylate, Dimethicone?/inyl Dimethicone Crosspolymer, Dimethicone/Vinyltrimethylsiloxysilicate Crosspolymer, Dimethiconol, Dimethiconol Arginine, Dimethiconol Beeswax, Dimethiconol Behenate, Dimethiconol Borageate, Dimethiconol Candelillate, Dimethiconol Carnaubate, Dimethiconol Cysteine, Dimethiconol Dhupa Butterate, Dimethiconol Fluoroalcohol Dilinoleic Acid, Dimethiconol Hydroxystearate, Dimethiconol Illipe Butterate, Dimethiconol/IPDI Copolymer, Dimethiconol Isostearate, Dimethiconol Kokum Butterate, Dimethiconol Lactate, Dimethiconol Meadowfoamate, Dimethiconol Methionine, Dimethiconol/Methylsilanol/Silicate Crosspolymer, Dimethiconol Mohwa Butterate, Dimethiconol Panthenol, Dimethiconol Sal Butterate, Dimethiconol/Silica Crosspolymer, Dimethiconol/Silsesquioxane Copolymer, Dimethiconol Stearate, Dimethiconol/Stearyl, Methicone/Phenyl Trimethicone Copolymer, Dimethoxysilyl Ethylenediaminopropyl Dimethicone, Dimethylaminopropylamido PCA Dimethicone, Dimethyl Oxobenzo Dioxasilane, Dimethylsilanol Hyaluronate, Dioleyl Tocopheryl Methylsilanol, Diphenyl Amodimethicone, Diphenyl Dimethicone, Diphenyl Dimethicone Crosspolymer Diphenyl Dimethicone?/inyl Diphenyl Dimethicone/Silsesquioxane Crosspolymer, Diphenylethyl Benzyloxy Dilsiloxane, Diphenylisopropyl Dimethicone, Diphenylsiloxy Phenyl/Propyl Trimethicone, Diphenylsiloxy Phenyl Trimethicone Disiloxane, Disodium Amodimethicone Disuccinamide, Disodium PEG-12 Dimethicone Sulfosuccinate, Disodium PEG-8 Lauryl Dimethicone Sulfosuccinate, Divinyldimethicone/Dimethicone Copolymer, Divinyldimethicone/Dimethicone Crosspolymer, Drometrizole Trisiloxane, Ethylhexyl Acrylate/VP/Dimethicone Methacrylate Copolymer, Ethyl Methicone, Ethyl Trisiloxane, Fluoro C2-8 Alkyldimethicone, Gluconamidopropyl Aminopropyl Dimethicone, 4-(2-Beta-Glucopyranosiloxy) Propoxy-2-Hydroxybenzophenone, Glyceryl Undecyl Dimethicone, Glycidoxy Dimethicone, Hexadecyl Methicone, Hexyl Dimethicone, Hexyl Methicone, Hexyltrimethoxysilane, Hydrogen Dimethicone, Hydrogen Dimethicone/Octyl Silsesquioxane Copolymer, Hydrolyzed Collagen PG-Propyl Dimethiconol, Hydrolyzed Collagen PG-Propyl Methylsilanediol, Hydrolyzed Collagen PG-Propyl Silanetriol, Hydrolyzed Keratin PG-Propyl Methylsilanediol, Hydrolyzed Sesame Protein PG-Propyl Methylsilanediol, Hydrolyzed Silk PG-Propyl Methylsilanediol, Hydrolyzed Silk PG-Propyl Methylsilanediol Crosspolymer, Hydrolyzed Soy Protein/Dimethicone PEG-7 Acetate, Hydrolyzed Soy Protein PG-Propyl Methylsilanediol, Hydrolyzed Vegetable Protein PG-Propyl Silanetriol, Hydrolyzed Wheat Protein/Cystine Bis-PG-Propyl Silanetriol Copolymer, Hydrolyzed Wheat Protein/Dimethicone PEG-7 Acetate, Hydrolyzed Wheat Protein/Dimethicone PEG-7 Phosphate Copolymer, Hydrolyzed Wheat Protein PG-Propyl Methylsilanediol, Hydrolyzed Wheat Protein PG-Propyl Silanetriol, Hydroxyethyl Acetomonium PG-Dimethicone, Hydroxypropyldimethicone, Hydroxypropyl Dimethicone Behenate, Hydroxypropyl Dimethicone Isostearate, Hydroxypropyl Dimethicone Stearate, Isobutylmethacrylate/Bis-Hydroxypropyl Dimethicone Acrylate Copolymer, Isobutylmethacrylate/Trifluoroethylmethacrylate/Bis-Hydroxypropyl Dimethicone Acrylate Copolymer, Isopentyl Trimethoxycinnamate Trisiloxane, Isopolyglyceryl-3 Dimethicone, Isopolyglyceryl-3 Dimethiconol, Isopropyl Titanium Triisostearate/Triethoxysilylethyl, Polydimethylsiloxyethyl Dimethicone Crosspolymer, Isostearyl Carboxydecyl PEG-8 Dimethicone, Lactoyl Methylsilanol Elastinate, Lauryl Dimethicone, Lauryl Dimethicone PEG-15 Crosspolymer, Lauryl Dimethicone PEG-10 Phosphate, Lauryl Dimethicone/Polyglycerin-3 Crosspolymer, Lauryl Methicone, Lauryl PEG-8 Dimethicone, Lauryl PEG-10 Methyl Ether Dimethicone, Lauryl PEG-9 Polydimethylsiloxyethyl Dimethicone, Lauryl PEG/PPG-18/18 Methicone, Lauryl Phenylisopropyl Methicone, Lauryl Phenylpropyl Methicone, Lauryl Polydimethylsiloxyethyl Dimethicone/Bis-Vinyldimethicone Crosspolymer, Lauryl Polyglyceryl-3 Polydimethylsiloxy-ethyl Dimethicone, Lauryl Trimethicone, Linoleamidopropyl PG-Dimonium Chloride Phosphate Dimethicone, Methacryloyl Propyltrimethoxysilane, Methicone, Methoxy Amodimethicone/Silsesquioxane Copolymer, Methoxycinnamidopropyl Polysilsesquioxane, Methoxycinnamoylpropyl Silsesquioxane Silicate, Methoxy PEG-13 Ethyl Polysilsesquioxane, Methoxy PEG/PPG-7/3 Aminopropyl Dimethicone, Methoxy PEG/PPG-25/4 Dimethicone, Methoxy PEG-10 Propyltrimethoxysilane, Methyleugenyl PEG-8 Dimethicone, Methylpolysiloxane Emulsion, Methylsilanol Acetylmethionate, Methylsilanol Acetyltyrosine, Methylsilanol Ascorbate, Methylsilanol Carboxymethyl Theophylline, Methylsilanol Carboxymethyl Theophylline Alginate, Methylsilanol Elastinate, Methylsilanol Glycyrrhizinate, Methylsilanol Hydroxyproline, Methylsilanol Hydroxyproline Aspartate, Methylsilanol Mannuronate, Methylsilanol PCA, Methylsilanol PEG-7 Glyceryl Cocoate, Methylsilanol/Silicate Crosspolymer, Methylsilanol Spirulinate, Methylsilanol Tri-PEG-8 Glyceryl Cocoate, Methyl Trimethicone, Methyltrimethoxysilane, Myristylamidopropyl Dimethylamine Dimethicone PEG-7 Phosphate, Myristyl Methicone, Myristyl Trisiloxane, Nylon-611/Dimethicone Copolymer, PCA Dimethicone, PEG-7 Amodimethicone, PEG-8 Amodimethicone, PEG-8 Cetyl Dimethicone, PEG-3 Dimethicone, PEG-6 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG-10 Dimethicone Cross-polymer, PEG-12 Dimethicone Crosspolymer, PEG-8 Dimethicone Dimer Dilinoleate, PEG-8 Dimethicone/Dimer Dilinoleic Acid Copolymer, PEG-10 Dimethicone/Vinyl Dimethicone Crosspolymer, PEG-8 Distearmonium Chloride PG-Dimethicone, PEG-10/Lauryl Dimethicone Crosspolymer, PEG-15/Lauryl Dimethicone Crosspolymer, PEG-15/Lauryl Polydimethylsiloxyethyl Dimethicone Crosspolymer, PEG-8 Methicone, PEG-6 Methicone Acetate, PEG-6 Methyl Ether Dimethicone, PEG-7 Methyl Ether Dimethicone, PEG-8 Methyl Ether Dimethicone, PEG-9 Methyl Ether Dimethicone, PEG-10 Methyl Ether Dimethicone, PEG-11 Methyl Ether Dimethicone, PEG-32 Methyl Ether Dimethicone, PEG-8 Methyl Ether Triethoxysilane, PEG-10 Nonafluorohexyl Dimethicone Copolymer, PEG-4 PEG-12 Dimethicone, PEG-8 PG-Coco-Glucoside Dimethicone, PEG-9 Polydimethylsiloxyethyl Dimethicone, PEG/PPG-20/22 Butyl Ether Dimethicone, PEG/PPG-22/22 Butyl Ether Dimethicone, PEG/PPG-23/23 Butyl Ether Dimethicone, PEG/PPG-24/18 Butyl Ether Dimethicone, PEG/PPG-27/9 Butyl Ether Dimethicone, PEG/PPG-3/10 Dimethicone, PEG/PPG-4/12 Dimethicone, PEG/PPG-6/4 Dimethicone, PEG/PPG-6/11 Dimethicone, PEG/PPG-8/14 Dimethicone, PEG/PPG-8/26 Dimethicone, PEG/PPG-10/2 Dimethicone, PEG/PPG-12/16 Dimethicone, PEG/PPG-12/18 Dimethicone, PEG/PPG-14/4 Dimethicone, PEG/PPG-15/5 Dimethicone, PEG/PPG-15/15 Dimethicone, PEG/PPG-16/2 Dimethicone, PEG/PPG-16/8 Dimethicone, PEG/PPG-17/18 Dimethicone, PEG/PPG-18/6 Dimethicone, PEG/PPG-18/12 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, PEG/PPG-30/10 Dimethicone, PEG/PPG-25/25 Dimethicone/Acrylates Copolymer, PEG/PPG-20/22 Methyl Ether Dimethicone, PEG/PPG-24/24 Methyl Ether Glycidoxy Dimethicone, PEG/PPG-10/3 Oleyl Ether Dimethicone, PEG/PPG-5/3 Trisiloxane, PEG-4 Trifluoropropyl Dimethicone Copolymer, PEG-8 Trifluoropropyl Dimethicone Copolymer, PEG-10 Trifluoropropyl Dimethicone Copolymer, PEG-8 Trisiloxane, Perfluorocaprylyl riethoxysilylethyl Methicone, Perfluorononyl Dimethicone, Perfluorononyl Dimethicone/Methicone/Amodimethicone Crosspolymer, Perfluorononylethyl Carboxydecyl Behenyl Dimethicone, Perfluorononylethyl Carboxydecyl Hexacosyl Dimethicone, Perfluorononylethyl Carboxydecyl Lauryl/Behenyl Dimethicone, Perfluorononylethyl Carboxydecyl Lauryl Dimethicone, Perfluorononylethyl Carboxydecyl PEG-8 Dimethicone, Perfluorononylethyl Carboxydecyl PEG-10 Dimethicone, Perfluorononylethyl Dimethicone/Methicone Copolymer, Perfluorononylethyl PEG-8 Dimethicone, Perfluorononylethyl Stearyl Dimethicone, Perfluorooctylethyl/Diphenyl Dimethicone Copolymer, Perfluorooctylethyl Triethoxysilane, Perfluorooctylethyl Trimethoxysilane, Perfluorooctylethyl Trisiloxane, Perfluorooctyl Triethoxysilane, PG-Amodimethicone, Phenethyl Dimethicone, Phenethyl Disiloxane, Phenyl Dimethicone, Phenylisopropyl Dimethicone, Phenyl Methicone, Phenyl Methiconol, Phenylpropyldimethylsiloxysilicate, Phenylpropyl Ethyl Methicone, Phenyl Propyl Trimethicone, Phenyl Propyl Trimethicone/Diphenylmethicone, Phenyl Trimethicone, Platinum Divinyldisiloxane, Polyacrylate-6, Polydiethylsiloxane, Polydimethylsiloxyethyl Dimethicone/Bis-Vinyldimethicone Crosspolymer, Polydimethylsiloxyethyl Dimethicone/Methicone Copolymer, Polydimethylsiloxy PEG/PPG-24/19 Butyl Ether Silsesquioxane, Polydimethylsiloxy PPG-13 Butyl Ether Silsesquioxane, Polyglyceryl-3 Disiloxane Dimethicone, Polyglyceryl-3/Lauryl Polydimethylsiloxyethyl Dimethicone Crosspolymer, Polyglyceryl-3 Polydimethylsiloxyethyl Dimethicone, Poly(Glycol Adipate)/Bis-Hydroxyethoxypropyl Dimethicone Copolymer, Polymethylsilsesquioxane, Polymethylsilsesquioxane/Trimethylsiloxysilicate, Polyphenylsilsesquioxane, Polypropylsilsesquioxane, Polysilicone-1, Polysilicone-2, Polysilicone-3, Polysilicone-4, Polysilicone-5, Polysilicone-6, Polysilicone-7, Polysilicone-8, Polysilicone-9, Polysilicone-10, Polysilicone-11, Polysilicone-12, Polysilicone-13, Polysilicone-14, Polysilicone-15, Polysilicone-16, Polysilicone-17, Polysilicone-18, Polysilicone-19, Polysilicone-20, Polysilicone-21, Polysilicone-18 Cetyl Phosphate, Polysilicone-1 Crosspolymer, Polysilicone-18 Stearate, Polyurethane-10, Potassium Dimethicone PEG-7 Panthenyl Phosphate, Potassium Dimethic one PEG-7 Phosphate, PPG-12 Butyl Ether Dimethicone, PPG-2 Dimethicone, PPG-12 Dimethicone, PPG-27 Dimethicone, PPG-4 Oleth-10 Dimethicone, Propoxytetramethyl Piperidinyl Dimethicone, Propyl Trimethicone, Quaternium-80, Retinoxytrimethylsilane, Silanediol Salicylate, Silanetriol, Silanetriol Arginate, Silanetriol Glutamate, Silanetriol Lysinate, Silanetriol Melaninate, Silanetriol Trehalose Ether, Silica, Silica Dimethicone Silylate, Silica Dimethyl Silylate, Silica Silylate, Silicon Carbide, Silicone Quaternium-1, Silicone Quaternium-2, Silicone Quaternium-2 Panthenol Succinate, Silicone Quaternium-3, Silicone Quaternium-4, Silicone Quaternium-5, Silicone Quaternium-6, Silicone Quaternium-7, Silicone Quaternium-8, Silicone Quaternium-9, Silicone Quaternium-10, Silicone Quaternium-11, Silicone Quaternium-12, Silicone Quaternium-15, SiliconeQuaternium-16, Silicone Quaternium-16/Glycidoxy Dimethicone Crosspolymer, Silicone Quaternium-17, Silicone Quaternium-18, Silicone Quaternium-19, Silicone Quaternium-20, Silicone Quaternium-21, Silicone Quaternium-22, Silicone Quaternium-24, Silicone Quaternium-25, Siloxanetriol Alginate, Siloxanetriol Phytate, Simethicone, Sodium Carboxydecyl PEG-8 Dimethicone, Sodium Dimethicone PEG-7 Acetyl Methyltaurate, Sodium Hyaluronate Dimethylsilanol, Sodium Lactate Methylsilanol, Sodium Mannuronate Methylsilanol, Sodium PCA Methylsilanol, Sodium PG-Propyldimethicone Thiosulfate Copolymer, Sodium PG-Propyl Thiosulfate Dimethicone, Sodium Propoxyhydroxypropyl Thiosulfate Silica, Sorbityl Silanediol, Soy Triethoxysilylpropyldimonium Chloride, Stearalkonium Dimethicone PEG-8 Phthalate, Stearamidopropyl Dimethicone, Steardimonium Hydroxypropyl Panthenyl PEG-7 Dimethicone Phosphate Chloride, Steardimonium Hydroxypropyl PEG-7 Dimethicone Phosphate Chloride, Stearoxy Dimethicone, Stearoxymethicone/Dimethicone Copolymer, Stearoxytrimethylsilane, Stearyl Aminopropyl Methicone, Stearyl Dimethicone, Stearyl/Lauryl Methacrylate Crosspolymer, Stearyl Methicone, Stearyl Triethoxysilanek, Stearyl Trimethicone, Styrene/Acrylates/Dimethicone Acrylate Crosspolymer, Styrene/Acrylates/Dimethicone Copolymer, TEA-Dimethicone PEG-7 Phosphate, Tetrabutoxy-propyl Trisiloxane, Tetramethyl Hexaphenyl Tetrasiloxane, Tetramethyl Tetraphenyl Trisiloxane, Tocopheryloxypropyl Trisiloxane, Trideceth-9 PG-Amodimethicone, Triethoxycaprylylsilane, Triethoxysilylethyl Dimethicone/Methicone Copolymer, Triethoxysilylethyl Polydimethylsiloxyethyl Dimethicone, Triethoxysilylethyl Polydimethylsiloxyethyl Hexyl Dimethicone, Triethoxysilylpropylcarbamoyl Ethoxypropyl Butyl Dimethicone, Trifluoromethyl C1-4 Alkyl Dimethicone, Trifluoropropyl Cyclopentasiloxane, Trifluoropropyl Cyclotetrasiloxane, Trifluoropropyl Dimethicone, Trifluoropropyl Dimethicone/PEG-10 Crosspolymer, Trifluoropropyl Dimethicone/Trifluoropropyl Divinyldimethicone Crosspolymer, Trifluoropropyl Dimethicone/Vinyl Trifluoropropyl, Dimethicone/Silsesquioxane Crosspolymer, Trifluoropropyl Dimethiconol, Trifluoropropyldimethyl/trimethylsiloxysilicate, Trifluoropropyl Methicone, Trimethoxycaprylylsilane, Trimethoxysilyl Dimethicone, Trimethyl Pentaphenyl Trisiloxane, Trimethylsiloxyamodimethicone, Trimethylsiloxyphenyl Dimethicone, Trimethylsiloxysilicate, Trimethylsiloxysilicate/Dimethicone Crosspolymer, Trimethylsiloxysilicate/Dimethiconol Crosspolymer, Trimethylsiloxysilylcarbamoyl Pullulan, Trimethylsilyl Hydrolyzed Conchiolin Protein PG-Propyl Methylsilanediol Crosspolymer, Trimethylsilyl Hydrolyzed Silk PG-Propyl Methylsilanediol Crosspolymer, Trimethylsilyl Hydrolyzed Wheat Protein PG-Propyl Methylsilanediol Crosspolymer, Trimethylsilyl Pullulan, Trimethylsilyl Trimethylsiloxy Glycolate, Trimethylsilyl Trimethylsiloxy Lactate, Trimethylsilyl Trimethylsiloxy Salicylate, Triphenyl Trimethicone, Trisiloxane, Tris-Tributoxysiloxymethylsilane, Undecylcrylene Dimethicone, Vinyl Dimethicone, Vinyl Dimethicone/Lauryl Dimethicone Crosspolymer, Vinyl Dimethicone/Methicone Silsesquioxane Crosspolymer, Vinyldimethyl/Trimethylsiloxysilicate Stearyl Dimethicone Crosspolymer, VP/Dimethiconylacrylate/Polycarbamyl/Polyglycol Ester, Zinc Carboxydecyl Trisiloxane and Zinc Dimethicone PEG-8 Succinate and mixtures thereof.

More preferably the silicones to be contained in the mixture according to the inventions are Dimethicone, Cyclomethicone, Phenyl Trimethicone, Cyclohexasiloxane and Cyclopentasiloxane. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Filters

Primary sun protection filters in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

The UV filters cited below which can be used within the context of the present invention are preferred but naturally are not limiting. UV filters which are preferably used are selected from the group consisting of one, two, three, four, five or more of the following species:

| UV FILTER | TRADEMARK | SUPPLIER |
|---|---|---|
| 4-Methylbenzylidene Camphor | Neo Heliopan ® MBC | Symrise |
| Anthranilic Acid Menthyl Ester | Neo Heliopan ® MA | Symrise |
| Benzophenone-3 | Neo Heliopan ® BB | Symrise |
| Benzophenone-4 | Uvinul ® MS40 | BASF |
| Bis-Ethylhexyloxyphenol Methoxyphenyl Triazine | Neo Heliopan ® BMT | Symrise |
| Butyl Methoxydibenzoylmethane | Neo Heliopan ® 357 | Symrise |
| Diethylamine Hydroxybenzoyl Hexyl Benzoate | Uvinul ® A Plus | BASF |
| Diethylhexyl Butylamido Triazone | Iscotrizinol | 3V |
| Disodium Phenyl Dibenimidazole Sulfonic Acid | Neo Heliopan ® AP | Symrise |
| Ethylhexyl Methoxycinnamate | Neo Heliopan ® AV | Symrise |
| Ethylhexyl salicylate | Neo Heliopan ® OS | Symrise |
| Ethylhexyl triazone | Uvinul ® T150 | BASF |
| Homoslate | Neo Heliopan ® HMS | Symrise |
| Isoamyl p-Methoxycinnamate | Neo Heliopan ® E 1000 | Symrise |
| Methoxypropylamine Cyclohexenylidene Ethoxyethylcyanoacetate | | BASF |
| Methylene Bis-Benzotriazolyl Tetramethylbutylphhenol (nano) | Tinosorb ® M | BASF |
| Octocrylene | Neo Heliopan ® 303 | Symrise |
| Phenylbenzimidazole Sulfonic Acid | Neo Heliopan ® Hydro | Symrise |
| Phenylene Bis-Diphenyltriazone | Triasorb | Pierre Fabre |
| Polysilicone-15 | Parsol ® SLX | DSM |
| Tris-Biphenyl Triazine (nano) | Tinosorb ® A2B | BASF |

In a preferred embodiment the sun protection filter forming component (ii) represents a blend of UV-A- and UV-B-filters selected from the group consisting of homosalate, octocrylene, bis-ethylhexyloxyphenol methoxyphenyl triazine, butyl methoxydibenzoylmethane, ethylhexyl salicylate and mixtures thereof. Particular preferred is a blend of all these filters which is commercially available in the market under the trademark NeoHeliopan® Flat (SYMRISE), which also subject to WO 2020 088778 A1.

Suitable pigments encompass oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 5 and up to 50. Such formulations according to the invention are particularly suitable for protecting the skin and hair.

Secondary Sun Protection Filters

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodi-propionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Biogenic Agents and Antioxidants

Biogenic active substances include, for example, tocopherol, tocopherol acetate, tocopherol palmitate, ascorbic acid, (deoxy)ribonucleic acid and its fragmentation products, β-glucans, retinol, bisabolol, allantoin, phytantriol, panthenol, AHA acids, amino acids, ceramides, pseudoceramides, essential oils, plant extracts, such as such as prunus extract, bambaranus extract and vitamin complexes.

Antioxidants interrupt the photochemical reaction chain which is triggered when UV radiation penetrates the skin. Typical examples are amino acids (e.g. glycine, histidine, tyrosine, tryptophan) and their derivatives, imidazoles (e.g. urocanic acid) and their derivatives, peptides like D,L-carnosine, D-carnosine, L-carnosine and their derivatives (e.g. anserine), carotenoids, carotenes (e.g. -carotene, lycopene) and their derivates, chlorogenic acid and its derivatives, lipoic acid and its derivatives (e.g. dihydrolic acid), aurothioglucose, propylthiouracil and other thiols (e.g. thioredoxin, glutathione, cysteine, cystine, cystamin and their glycosyl, N-acetyl, methyl, ethyl, propyl, amyl, butyl and lauryl, palmitoyl, oleyl, linoleyl, cholesteryl and glyceryl esters) and their salts Dilaurylthiodipropionate, ditearylthiodipropionate, thiodipropionic acid and its derivatives (esters, ethers, peptides, lipids, nucleotides, nucleosides and salts) as well as sulfoximine compounds (e.g. (e.g. buthionine sulfoximines, homocysteine sulfoximines, butionine sulfones, penta-, hexa-, heptathionine sulfoximines) in very low tolerated dosages (e.g. pmol to mol/kg), furthermore (metal) chelators (e.g. hydroxy fatty acids, palmitic acid, phytinic acid, lactoferrin), hydroxy acids (e.g. (e.g. citric acid, lactic acid, malic acid), humic acid, gallic acid, bile extracts, bilirubin, biliverdin, EDTA, EGTA and their derivatives, unsaturated fatty acids and their derivatives (e.g. linolenic acid, linoleic acid, oleic acid), folic acid and its derivatives, ubiquinone and ubiquinol and their derivatives, vitamin C and its derivatives (e.g. ascorbyl palmitate, Mg-ascorbyl phosphate, ascorbylacetate), tocopherols and derivatives (e.g. vitamin E acetate), vitamin A and derivates (vitamin A palmitate) as well as conifer aryl benzoate of benzoic resin, rutinic acid and its derivatives, glycosylrutin, ferulic acid, furfurylidene glucitol, carnosine, butyl hydroxytoluene, butylhydroxyanisole, nordihydroguaiac resin acid, nordihydroguajaretic acid, trihydroxybutyrophenone, uric acid and its derivatives, mannose and its derivatives, superoxide dismutase, zinc and its derivatives (e.g. e.g. ZnO, ZnSO4) selenium and its derivatives (e.g. selenium-methionine), stilbenes and their derivatives (e.g. styrene oxide, trans-stilbene oxide) and the derivatives suitable for the invention (salts, esters, ethers, sugars, nucleotides, nucleosides, peptides and lipids) of these named active substances.

Actives Modulating Hair Pigmentation

Preferred active ingredients for hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivetives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of rumex and ramulus species, extracts of pine species (pinus), extracts of vitis species or stilbene derivatives isolated or concentrated therefrom, saxifrage extract, scutelleria extract, grape extract and/or microalgae extract, in particular Tetraselmis suecica Extract.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the chrysanthemum species, san-guisorba species, walnut extracts, urucum extracts, rhubarb extracts, microalgae extracts, in particular lsochrysis galbana, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (Leontodon or Taraxacum), Orthosiphon, Vitex, Coffea, Paullinia, Theobroma, Asiasarum, Cucurbita or Styphnolobium, Serenoa repens (saw palmetto), Sophora flavescens, Pygeum africanum, Panicum miliaceum, Cimicifuga racemosa, Glycine max, Eugenia caryophyllata, Cotinus coggygria, Hibiscus rosasinensis, Camellia sinensis, Ilex paraguariensis, lsochrysis galbana, licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera Chondrus, Gloiopeltis, Ceramium, Durvillea, Glycine max, Sanguisorba officinalis, Calendula officinalis, Hamamelis virginiana, Arnica montana, Salix alba, Hypericum perforatum or Gymnema sylvestre.

Physiological Cooling and Warming Agents

The physiological cooling agents are preferably selected from the group formed by the species depicted in the following table (including their optical isomers and racemates):

| Component | FEMA/GRAS | Trademark | Supplier |
|---|---|---|---|
| Menthol | | | |
| Menthol glyceryl acetal | 3807 | Frescolat° MGA | Symrise AG |
| Menthol glyceryl ketal | 3808 | Frescolat° MGA | Symrise AG |
| Menthol menthyl ether | | | |
| Menthone glyceryl acetal | | | |
| Menthone glyceryl ketal | | | |
| Menthoxy-1,2-propandiol | 3784 | | |
| Menthoxy-2-methyl-1,2-propanediol | 3849 | | |
| Menthyl acetate | | SymFresh° RF | Symrise AG |
| Menthyl ethylene glycol carbonate | 3805 | Frescolat° MGC | Symrise AG |
| Menthyl formiate | | | |
| Menthyl glutamate | 4006 | | |
| Menthyl glycerol carbonate | | | |
| Menthyl hydroxy isobutyrate | | | |
| Menthyl isobutyrate | | | |
| Menthyl lactate | | Frescolat° ML | Symrise AG |
| Menthyl malonate | | | |
| Menthyl methyl ether | | | |
| Menthyl N-ethyl oxamate | | | |
| Menthyl propylene glycol carbonate | 3806 | Frescolat° MPC | Symrise AG |
| Menthyl pyroglutamate | | | |
| Menthyl-(2-methoxy)acetate | | | |
| Menthyl-(2-methoxyethoxy)acetate | | | |
| Menthyl succinate | 3810 | | |
| O-Menthyl succinic acid ester amide | | | |
| O-Menthyl succinic acid ester-NN-(dimethyl)amide | | | |
| Menthane carboxylic acid-N-(4-cyanophenyl)amide | | | |
| Menthane carboxylic acid-N-(4-cyanomethyl-phenyl)amide | | | |
| Menthane carboxylic acid-N-ethylamide (WS-3) | | | |
| (WS-4) | | | |
| N$^\alpha$-(menthane carbonyl) glycine ethylester (WS-5) | | | |
| (1R,2S,5R)-N-(4-Methoxyphenyl)-5-methyl-2-(1-isopropyl)cyclohexane-carboxamide (WS-12) | | | |
| (WS-14) | | | |
| 2,3-dimethyl-2-(2-propyl)-butyric acid-N-methylamide (WS23) | | | |
| Isopulegol acetate | | | |
| p-Menthane-3,8-diol | | | |
| Cubebol | | | |
| 3-Methyl-2(1-pyrrolidinyl)-2-cyclopentene-1-one) | | | |
| Tetrahydropyrimidine-2-one | | | |
| N-(2-(pyridin-2-yl)ethyl)-3-p-menthane-carboxamide | | | |
| [(1R,2S,5R)-2-isopropyl-5-methyl-cyclohexyl] 2-(ethylamino)-2-oxo-acetate | | X Cool | Symrise AG |

Physiological warming agents can be selected from the group consisting of capsaicin, dihydrocapsaicin, nordihydrocapsaicin, homocapsaicin, homodihydrocapsaicin nonivamid, and chili extracts.

Anti-Inflammatory Agents

Suitable anti-inflammatory agents may be selected from the group formed by:
(i) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone,
(ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone,
(iii) natural or naturally occuring anti-inflammatory substances or substances that alleviate reddening and/or itching, in particular extracts or fractions from camomile, Aloe vera, Commiphora species, Rubia species, willow, willow-herb, oats, calendula, arnica, St John's wort, honeysuckle, rosemary, Passiflora incarnata, witch hazel, ginger or Echinacea, or single active compounds thereof, (iv) histamine receptor antagonists, serine protease inhibitors (e.g. of Soy extracts), TRPV1 antagonists (e.g. 4-t-Butylcyclohexanol), NK1 antagonists (e.g. Aprepitant, Hydroxyphenyl Propamidobenzoic Acid), cannabinoid receptor agonists (e.g. Palmitoyl Ethanolamine) and TRPV3 antagonists.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxy-ethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odourneutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxy-allantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival® (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}-piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives and/or Product Protection Agents

Suitable preservatives are listed in Appendix 6, Parts A and B of the Kosmetikverordnung ("Cosmetics Directive").

Suitable species can be selected from the group consisting of preservatives selected from the group consisting of benzoic acid and para-hydroxybenzoic acid, their esters and salts, benzyl benzoate, propionic acid and its salts, salicylic acid and its salts, 2,4-hexadienoic acid (sorbic acid) and its salts, levulinic acid and its salts, anisic acid and its salts, perillic acid and its salts, cinnamic acid and its salts, formaldehyde and paraformaldehyde, 4-hydroxy benzaldehyde, ortho-, meta-, and para-anisic aldehyde, cinnamic aldehyde, cinnamic alcohol, 2-hydroxybiphenyl ether and its salts, 2-zinc-sulfidopyridine N-oxide, inorganic sulfites and bisulfites, sodium iodate, chlorobutanolum, 4-ethylmercury-(II)5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury-(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxy-diphenyl ether, 4-chloro-3,5-dimethylphenol, 1,1'-methylene-bis(3-(1-hydroxymethyl-2,4-dioximidazolidin-5-yl)urea), poly-(hexamethylenediguanide) hydrochloride, (Benzyloxymethoxy)-methanol hexamethylenetetramine, 1-(3-chloroallyl)-3,5,7-triaza-1-azonia-adamantane chloride, 1-(4-chlorophenoxy)-1-(1H-imidazol-1-yl)-3,3-dimethyl-2-butanone, 1,3-bis-(hydroxymethyl)-5,5-dimethyl-2,4-imidazolidinedione, 1,2-dibromo-2,4-dicyanobutane, 2,2'-methylene-bis(6-bromo-4-chlorophenol), bromochlorophene, mixture of 5-chloro-2-methyl-3(2H)-isothiazolinone, 2-methyl-3(2H)-isothiazolinone and with magnesium chloride and magnesium nitrate, 2-Octyl-2H-isothiazol-3-one, 1,2-benzisothiazol-3(2H)-one, 2-benzyl-4-chlorophenol, 3-(4-Chlorphenoxy)-1,2-propanediol (Chlorphenesin), 2-chloroacetamide, chlorhexidine, chlorhexidine acetate, chlorhexidine gluconate, chlorhexidine hydrochloride, N-alkyl($C_{12}$-$C_{22}$)trimethyl-ammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxy-methylurea, 1,6-bis(4-amidino-phenoxy)-n-hexane and its salts, glutaraldehyde, 5-ethyl-1-aza-3,7-dioxabicyclo(3.3.0)octane, 3-(4-chlorophenoxy)-1,2-propanediol, hyamines, alkyl-($C_8$-$C_{18}$)-dimethyl-benzyl-ammonium chloride, alkyl-($C_8$-$C_{18}$)-dimethyl-benzylammonium bromide, alkyl-($C_8$-$C_{18}$)-dimethyl-benzyl-ammonium saccharinate, benzyl hemiformal, 3-iodo-2-propynyl butylcarbamate, sodium hydroxymethyl-aminoacetate or sodium hydroxymethyl-aminoacetate, imidazolidinylurea, diazolidinylurea, sodium hydroxymethyl-glycinate, DMDM hydantoin, Tropolone, (Ethylendioxy) dimethanol, 2-Brom-2-(brommethyl)pentandinitril, N-(3-Aminopropyl)-N-dodecylpropan-1,3-diamin, α,α',α''-trimethyl-1,3,5-triazine-1,3,5(2H,4H,6H)-triethanol, pyridine-2-thiol-1-oxide, sodium salt, Tetrahydro-1,3,4,6-tetrakis(hydroxymethypimidazo[4,5-d]imidazol-2,5(1H, 3H)-dion, 1,3-bis(hydroxymethyl)-1-(1,3,4-tris(hydroxymethyl)-2,5-dioxoimidazolidin-4-yl)urea (Diazolidinyl Urea), 1,3-Bis(hydroxy-methyl)-5,5-dimethylimid azolidine-2,4-dione, 3-Acetyl-2-hydroxy-6-methyl-4H-pyran-4-one, cetyl pyridium chloride, caprylhydroxamic acid, sorbohydroxamic acid and their mixtures; 1,3-propanediol, methyl propanediol, 1,2-pentanediol, 1,2-hexanediol, 1,2-octanediol, 1,2-decanediol, 1,5-pentanediol, 1,6-hexanediol, 1,8-octanediol, 1,2-decanediol, ethylhexylglycerin, hexoxy-propan-1,2-diol, heptoxy-propan-1,2-diol, octoxy-propan-1,2-diol, 3-phenoxypropan-1,2-diol, 3-benzyloxy-propan-1,2-diol, 3-phenylethyloxy-propan-1,2-diol, 3-phenylpropyloxy-propan-1,2-diol, 3-methylbenzyloxy-propan-1,2-diol, sorbitan caprylate, triclosan, climbazole, Octopirox (1-hydroxy-4-methyl-6-(2,4,4-trimethylpentyl)-2 (1H)-pyridone, 2-aminoethanol), chitosan, farnesol, 2-butyloctanoic acid, 2-Benzylheptan-1-ol, glycerol monolaurate, bis(2-pyridylthio)zinc 1,1'-dioxide, N,N'-(decane-1,10-diyl-dipyridin-1-yl-4-ylidene)-dioctan-1-amine dihydrochloride (octenidine dihydrochloride), thymol, eugenol, benzyl alcohol, 2-phenyethyl alcohol, 3-phenyl propanol, 2-phenoxy-ethanol, 1-phenoxypropan-2-ol, 3-phenoxypropanol, benzyloxymethanol, 4-hydroxyacetophenone and mixtures thereof.

Perfume Oils

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used.

Fragrances with Woody Odor

Suitable fragrances with woody odor are selected from the group consisting of:

| INCI | Tradename | Supplier |
|---|---|---|
| (Ethoxymethoxy)cyclododecane | AMBERWOOD ® | Symrise |
| β-2,2,3-Tetramethylcyclopent-3-ene-1-butanol | BRAHMANOL ® | Symrise |
| alpha-Ethyl-2,2,6-trimethylcyclohexanepropanol | MADRANOL ® | Symrise |
| Octahydro-4,7-methano-1H-indenemethyl acetate | MYROSE ® ACETATE | Symrise |
| 1,1-Dimethoxy-cyclododecane | PALISANDAL ® | Symrise |
| Methoxycyclododecane | PALISANDIN ® | Symrise |
| (2E)-2-Ethyl-4-(2,2,3)-trimethylcyclopent-3-en-1-yl) but-2-en-1-ol | SANDRANOL ® | Symrise |
| 2H-2,4a-Methanonaphthalene, 1,3,4,5,6,7-hexahydro-7-methoxy-1,1,5,5-tetramethyl-4-Methyl-4-phenylpentan-2-one | SYMROXANE ® | Symrise |
| 4-Cyclohexyl-4-methylpentan-2-one | VETIKON ® | Symrise |
| | VETIRAL ® | Symrise |
| 1',1',5,5'-Tetramethylhexahydro-spiro[1,3-dioxolane-2,8'(5'H)-2H-2,4a-methanonaphthalene] | YSAMBER ® K | Symrise |

Fragrances with Amber Odor

Suitable fragrances with amber odor are selected from the group consisting of:

| INCI | Tradename | Supplier |
|---|---|---|
| (4aR,5R,7aS,9R)-Octahydro-2,2,5,8,8,9a-hexamethyl-4H-4a,9-methanoazuleno[5,6-d]-1,3-dioxole | AMBROCENIDE ® | Symrise |
| 3a,6,6,9a-Tetramethyl-dodecahydronaphtho[2,1-b]furan | AMBROXIDE ® | Symrise |

Fragrances with Fruity Odor

Suitable fragrances with fruity odor are selected from the group consisting of:

| INCI | Tradename | Supplier |
|---|---|---|
| Acetophenone | | Symrise |
| 2-tert.-butyl cyclohexyl acetate | AGRUMEX ® HC | Symrise |
| Octadecanal | ALDEHYDE C18 | Symrise |
| Allyl caproate | | Symrise |
| Allyl cyclohexyl propionate | | Symrise |
| Allyl heptoate | | Symrise |
| Allyl phenoxy acetal | | Symrise |
| 5-Hexyldihydro-4-methylfuran-2(3H)-one | APRIFLOREN ® | Symrise |
| Benzaldehyde | | Symrise |
| Benzyl alcohol | | Symrise |
| 1,5-Dimethyl-bicyclo[3.2.1]octan-8-one oxime | BUCCOXIME ® | Symrise |
| 1-Cyclohexylethyl-2-butenoate | DATILAT ® | Symrise |
| 3,7-Dimethyloct-1,6-diene | DIHYDROMYRCENE | Symrise |
| Ethyl acetoacetate | | Symrise |
| Ethyl butyrate | | Symrise |
| Ethyl caproate | | Symrise |
| Ethyl heptoate | | Symrise |
| Ethyl isovalerate | | Symrise |
| Ethyl methyl butyrate-2 | | Symrise |
| Ethyl propionate | | Symrise |
| (2E)-5-Methylhept-2-en-4-one | FILBERTONE ® | Symrise |
| 2,4,6-Trimethyl-4-phenyl-1,3-dioxane | FLOROPAL ® | Symrise |
| Ethyl 2,4-dimethyl-1,3-dioxolane-2-acetate | FRAGOLANE ® | Symrise |
| 4-(4-Methoxyphenyl)butan-2-one | FRAMBION METHL ETHER | Symrise |

-continued

| INCI | Tradename | Supplier |
|---|---|---|
| 1,3-Dimethylbutyl 2-butenoate | FRUTINAT ® | Symrise |
| Hexyl acetate | | Symrise |
| Isoamyl butyrate | | Symrise |
| Isoamyl isovalerate | | Symrise |
| (2E)-1-(2,4,4-Trimethylcyclohex-2-en-1-yl) but-2-en-1-one | ISODAMASCONE | Symrise |
| Ethyl (2-methyl-1,3-dioxolan-2-yl)acetate | JASMAPRUNAT ® | Symrise |
| Methyl phenyl acetate | | Symrise |
| 6-Butyl-tetrahydro-pyran-2-one | NONALACTONE DELTA | Symrise |
| 2-Methyl-4-propyl-[1,3]-oxathiane | OXANTHIA ® | Symrise |
| 1,1'-Bi(cyclopentyl)-2-yl (2E)-but-2-enoate | PYROPRUNAT ® | Symrise |
| 2-Cyclopentene-1-acetic acid, ethyl ester | SULTANENE ® | Symrise |
| rel-(2R,4S,6R)-2,4,6-Trimethyl-4-phenyl-1,3-dioxane | VERTACETAL ® COEUR | Symrise |
| 1,3-Dimethyl-3-phenylbutylacetate | VERTICOLACETAT ® | Symrise |

Fragrances with Musk Odor

Suitable fragrances with musk odor are selected from the group consisting of:

| INCI | Tradename | Supplier |
|---|---|---|
| Oxacycloheptadec-10-en-2-one | AMBRETTOLIDE ® | Symrise |
| Cyclohexadec-8(7)-en-1-one | AURELIONE ® | Symrise |
| Oxacyclohexadecen-2-one | GLOBALIDE ® | Symrise |
| Cyclohexadec-8-en-1-one | GLOBANONE ® | Symrise |
| Cyclohexadecanone | ISOMUSCONE | Symrise |
| Oxacyclohexadecan-2-one | MACROLIDE ® | Symrise |
| Pentadecan-15-olide | MACROLIDE ® SUPRA | Symrise |
| 1,4-Dioxacycloheptadecan-5,17-dion | ETHYLENE BRASSYLATE | Merck |

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO(OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds stay on the skin and/or hair for a longer period of time, compared to rinse-off products).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), eau de perfume, eau de toilette, after-shave, a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and after-shave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99 wt.-percent., preferably from about 5 to about 80 wt.-percent and more preferably either from about 10 to about 50 or from about 60 to about 80 wt.-percent based on the total weight of the preparation.

DETAILED DESCRIPTION

Figure 1:
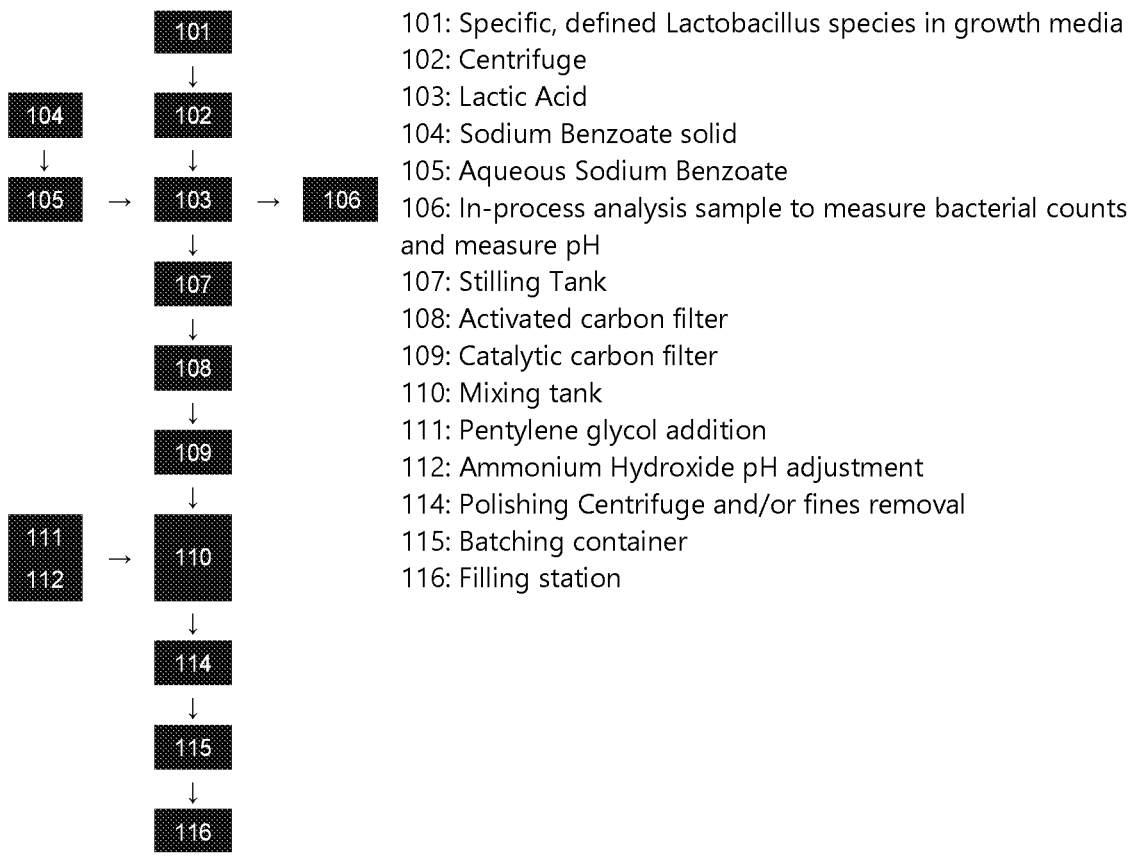
FIG. 1 shows a flow scheme according to the invention.
Figure 2:
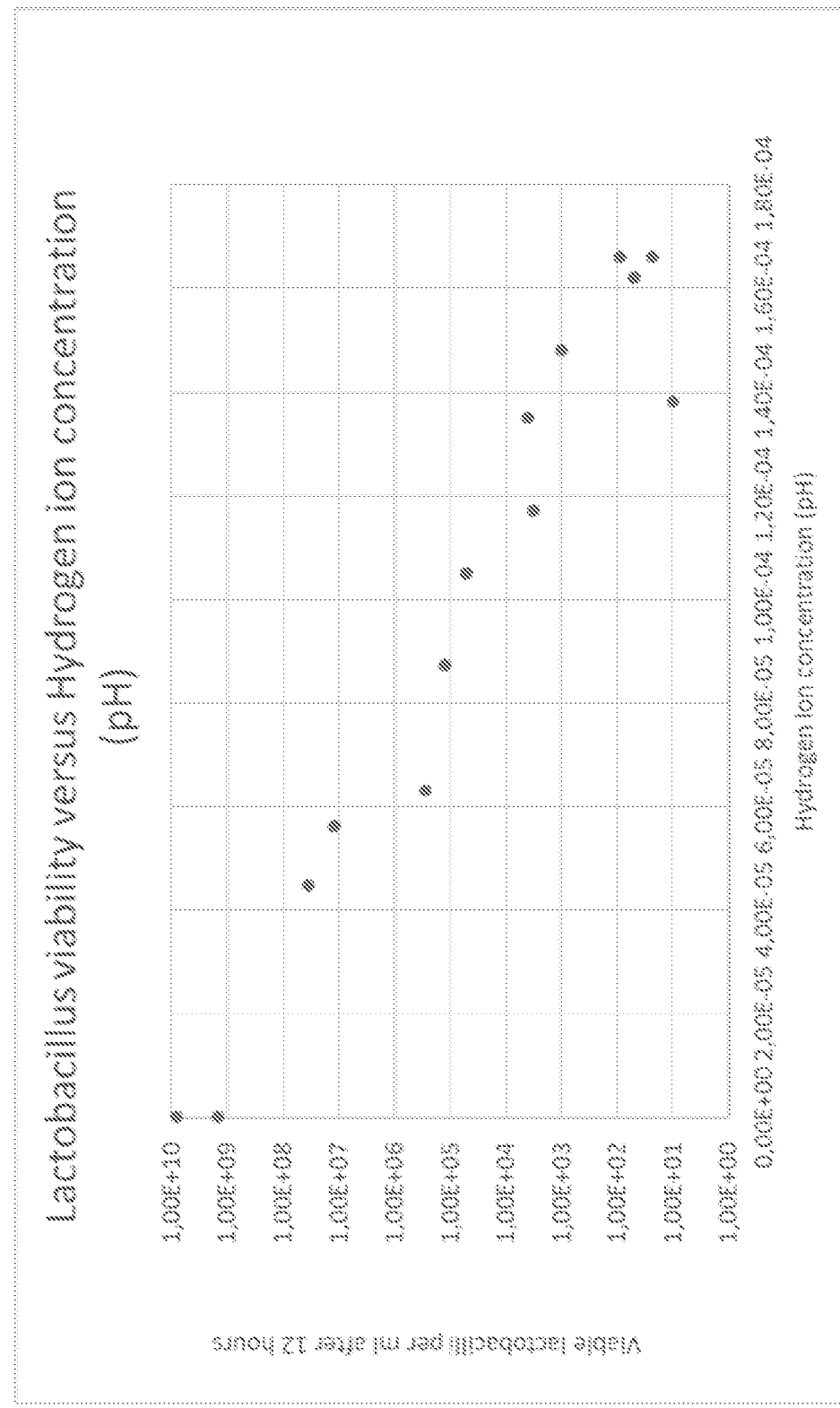
FIG. 2 shows the viability vs. lactic acid addition of the bacterial ferment.
Figure 3:
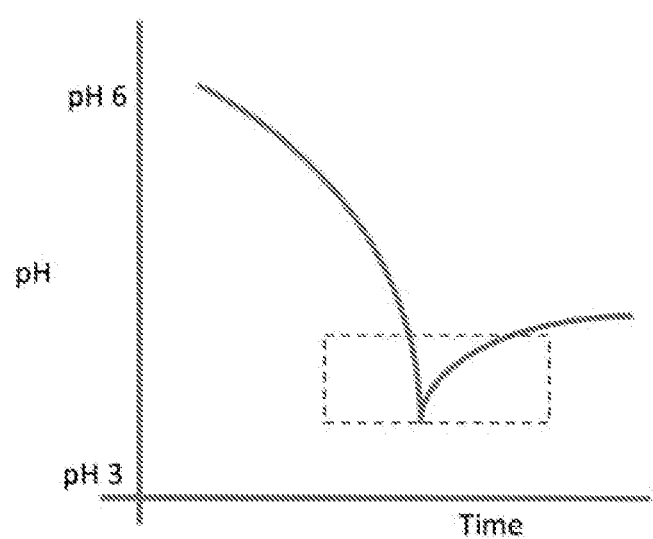
FIG. 3 shows the pH reflex response and time.

The following examples are intended to illustrate the present invention without limiting the invention. Unless indicated otherwise all amounts, parts and percentages are based on the weight and the total amount or on the total weight and the total amount of the preparations.
Processes and Characteristics of Lactic Acid Bacteria Ferments Example 1

*Lactobacillus plantarum* was inoculated from a 1 ml frozen seed stock and grown under sterile, aseptic conditions at 37 centigrade in 1 liter growth medium, then transferred to 400-liter intermediate growth medium after 24 hours and then transferred to a 5000 liter culture vessel after a subsequent phase of growth at 24 hours. The bacterial growth medium consisted of a blend of yeast extract, yeast peptone, sodium acetate, dextrose, sucrose, ammonium citrate, potassium phosphate, ascorbic acid, L-cysteine, magnesium sulfate, tween-80 and water. 5000 litres of a light brown, pungent smelling, growth media containing *Lactobacillus plantarum* that had just reached the stationary growth phase was separated by centrifugation in a sterile disc stack centrifuge. The supernatant from the centrifugation step was depleted of bacteria, however it still contained 3,500,000 lactobacilli per ml. Sodium benzoate was added during the collection process to a final concentration of 0.5%. Then, 70 liters of 88% aqueous lactic acid was mixed into to the supernatant and the mixture allowed to incubate at room temperature for 48 hours. The ferment was then blended with ferment derived from *Lactobacillus casei* prepared with the same process of centrifugation, addition of sodium benzoate and pH shock to produce a mixture of materials from different probiotic species. This mixture was then passed through an activated carbon filter, this carbon treated mixture was then passed through a catalytic carbon filter and the resulting treated mixture collected in a stilling tank. After 8 hours an aqueous mixture of 2% pentylene glycol was added to the mixture in the stilling tank and mixed then 30% ammonium hydroxide is added in a stepwise fashion until the pH reached 4.6. The mixture was centrifuged through a high g-force clarifying centrifuge to remove any final precipitation. The decanted supernatant was filtered through a 0.2 micron filter before being filled into 25 L screw cap containers.

Example 2

*Lactobacillus gasseri* was inoculated from a 1 ml frozen seed stock and grown under sterile, aseptic conditions at 37 centigrade in 1 liter growth medium, then transferred to 400 liter intermediate growth medium after 24 hours and then transferred to a 5000 liter culture vessel after a subsequent phase of growth at 24 hours. The bacterial growth medium consisted of a blend of yeast extract, yeast peptone, sodium acetate, dextrose, sucrose, ammonium citrate, potassium phosphate, ascorbic acid, L-cysteine, magnesium sulfate, tween-80 and water. 5000 liters of a dark brown, pungent smelling, growth media containing *Lactobacillus gasseri* that had just reached the stationary growth phase was separated by centrifugation in a sterile disc stack centrifuge. The supernatant from the centrifugation step was depleted of bacteria, however it still contained 1,500,000 lactobacilli per ml. Sodium benzoate was added during the collection process to a final concentration of 0.5%. Then, 70 liters of 88% aqueous lactic acid was mixed into to the supernatant and the mixture allowed to incubate at room temperature for 48 hours. This mixture was then passed through an activated carbon filter, this carbon treated mixture was then passed through a catalytic carbon filter. To further decolor the material was passed through an additional filter containing granulated manganese dioxide to remove excess tannins and the resulting treated mixture collected in a stilling tank. After 8 hours an aqueous mixture of 2% pentylene glycol was added to the mixture in the stilling tank and mixed then 30% ammonium hydroxide is added in a stepwise fashion until the pH reached 4.6. After a stilling period of 48 hours the clarified mixture was centrifuged through a high g-force clarifying centrifuge and the resulting supernatant clarified by diatomaceous earth filtration to remove any final precipitation. The decanted supernatant was filtered through a 0.2 micron filter before being filled into 25 L screw cap containers.

Example 3

The following bacterial strains were prepared under sterile conditions and grown individually each at a scale of 5000-liter fermentation: *Lactobacillus acidophilus, Lactobacillus casei, Lactobacillus fermenturn, Lactobacillus gasseri, Lactobacillus helveticus, Lactobacillus paracasei, Lactobacillus plantarum, Lactobacillus reuteri, Lactobacillus rhamnosus, Lactobacillus sakei* and *Lactobacillus salivarius*. Each strain was harvested individually by sterile centrifugation and the supernatant was treated with 0.5% sodium benzoate and 'shocked' with 5-8% lactic acid addition, followed by incubation at room temperature for 24 hours. The treated culture supernatant mixtures were then blended together to reach a specific colour hue specification of yellow. This mixture was then passed through an activated carbon filter, this carbon treated mixture was then passed through a catalytic carbon filter. An aqueous mixture of pentylene glycol was added to the mixture to reach a final concentration of 2% in the stilling tank and an ammonium hydroxide stock was added in a stepwise fashion until the pH reached 4.6. After a stilling period of 48 hours the clarified mixture was clarified by diatomaceous earth filtration to remove any final precipitation. The decanted supernatant was filtered through a 0.2 micron filter before being filled into 25 L screw cap containers.

Example 4 to 6, Comparison Examples C1 to C2

The following bacterial strains were prepared under sterile conditions and grown individually each at a scale of 5000 litre fermentation: *Lactobacillus acidophilus, Lactobacillus casei, Lactobacillus fermenturn, Lactobacillus gasseri, Lactobacillus helveticus, Lactobacillus paracasei, Lactobacillus plantarum, Lactobacillus reuteri, Lactobacillus rhamnosus, Lactobacillus sakei* and *Lactobacillus salivarius*. Each strain was harvested individually by sterile centrifugetion and the supernatant was treated with 0.5% sodium benzoate and treated with 3-5% lactic acid addition, followed by passing through a 20 kV electric field. The treated culture supernatant mixtures were then blended together to reach a specific color hue specification of yellow. This mixture was then passed through an activated carbon filter, this carbon treated mixture was then passed through a catalytic carbon filter. An aqueous mixture of pentylene glycol was added to the mixture to reach a final concentration of 2% in the stilling tank and an ammonium hydroxide stock was added in a stepwise fashion until the pH reached 4.6. After a stilling period of 48 hours the clarified mixture was clarified by diatomaceous earth filtration to remove any final precipitation. The decanted supernatant was filtered through a 0.2 micron filter before being filled into 25 L screw cap containers.

Modulation of Filaggrin Levels in Skin Explants

Filaggrins play a key role in the cornification process of the human epidermis by cross-linking keratins. Additionally, they can incorporate into the lipid envelope of keratinocytes, supporting its role as skin barrier to prevent moisture loss. Filaggrin can therefore be used as a marker for skin barrier function and terminal keratinocyte differentiation in the epidermis.

To test for potential modulation of filaggrin levels by the bacterial ferment according to the invention ( ), abdominal skin samples (from plastic surgery) from a female donor (born in 1993) were used after obtaining informed consent. The skin samples were characterized in terms of phototype and classified as "Light" (ITA°=43°). Skin samples were cut into pieces of approx. 8×3 mm (diameter×thickness) and placed on a perforated stainless-steel ring. Cultivation was carried out at an air-liquid interface using modified William's E medium. Six skin samples were used per treatment.

Test samples were applied topically to the tissue explants by first cleaning the skin surface with a cotton pad and subsequently applying 4 µl of test sample on top of the biopsies. Finally, the explant was covered with a delivery membrane (6 mm diameter). Application was performed daily from D0 to D5 (day 0 to day 5) of the organ culture.

On D6 of the experiment, the skin explants were harvested, fixated and sectioned (2 sections per explant) prior to immuno-staining with a specific antibody (Rabbit polyclonal anti-filaggrin, Santa Cruz, cat #sc30229). Detection was carried out using Dako REAL™ Detection System, Alkaline Phosphatase/RED, Rabbit/Mouse (Agilent, cat #K5005). The images of the slides were acquired and the signal was quantified by estimating the intensity and distribution of the pink/red staining within the epidermis using ImageJ (NIH, USA). Data were normalized to the dimension of the analysed skin surface (expressed in pixels).

In the experiment, the performance of the bacterial ferment according to the invention was evaluated vs PBS as vehicle control, as well as a sample of the culture broth prior to fermentation with Lactobacilli (Raw), a sample of raw medium containing the preservative system employed in the bacterial ferment according to the invention (2% Hydrolite-5), as well as a competitor benchmark product. Data for these treatments are summarized in Table 1

TABLE 1

Semi-quantitative evaluation of fillagrin modulation by the samples indicated in the table. Values shown are averages from 12 sections ± standard deviation. Statistical significance was tested using a t-test.

| Ex. | Sample | Average Filaggrin Score | SD | % Change vs Vehicle Control | p-value |
|---|---|---|---|---|---|
| 0 | PBS Vehicle | 2.34 | 0.92 | 0 | 1 |
| 0 | Raw Medium Control | 1.71 | 0.6 | −27 | 0.66 |
| 0 | Preservative Medium-Control | 2.47 | 0.67 | 1 | 1 |
| 4 | Bacterial ferment according to the invention | 5.29 | 1.54 | 126 | <0.01 |
| C1 | Competitor Benchmark | 2.27 | 1.42 | −3 | 0.62 |

Skin samples treated with the bacterial ferment according to the invention (Example 4) exhibited a clear and significant increase in fillaggrin levels (+126% vs vehicle control), whereas the controls and the competitor benchmark lowered filaggrin levels in skin explants or did not modulate them at all.

Modulation of Interleukin-8 Levels

Interleukin-8 (IL8) is an important intermediate signalling molecule in the response of tissues to insults, resulting in an inflammation reaction. As the phenomenon of irritated skin is tightly correlated to mild inflammatory conditions, levels of IL8 are being routinely used as biomarkers for irritation. IL8 is secreted by keratinocytes in the epidermis upon treatment with stresses such as UV light, chemical compounds or bacterial infection. IL8 is a chemoattractant which recruits other inflammatory cell types upon secretion.

To assess the effect of the bacterial ferment according to the invention on the secretion levels of IL8, reconstituted 3D skin models (EpiDerm™, MatTek) were used. After a short acclimation phase (daily medium changes), the models were switched to hydrocortisone-free medium, and test compounds were added topically to the reconstituted models. 50

μM dexamethasone was used as positive control, PBS served as negative control in the experiment. After 72 h incubation at 37° C. 5% CO2, the 3D models were washed with PBS and subsequently, an inflammatory response was stimulated by addition of 1 μg/ml Ma in the medium for approx. 24 h. Supernatants were collected after this phase and the IL8 concentration in these supernatants was determined using an ELISA kit (Human IL8/CXCL1 DuoSet ELISA, R&D Systems). To assess potential toxic effects of the test compounds on the 3D models, a standard MTT assay was carried out to assess viability of the 3D models at the end of the experiment. The results are shown in Table 2.

TABLE 2

IL8 concentrations in the supernatants of MatTek EpiDerm ™ 3D reconstituted skin models after treatment with test compounds and subsequent stimulation with 1 μg/ml IL1a. Values shown are averages from triplicates ± SEM. P-value is based on a T-test. Viability was determined using a standard MTT assay, values are normalized to stimulated control.

| Ex. | Sample | IL-8 concentration [pg/ml] ± SEM | p-value | Viability (% vs stimulated control) |
|---|---|---|---|---|
| | Unstimulated Control | 149 ± 7.88 | <0.01 | 105 |
| | Stimulated Control | 1552 ± 89.96 | 1 | 100 |
| | 50 μM Dexamethasone | 1225 ± 18.61 | 0.011 | 90 |
| | Raw Media Control | 2172 ± 127.57 | <0.01 | 114 |
| | Preservative Media Control | 1466 ± 63.9 | 0.385 | 126 |
| 5 | Bacterial ferment according to the invention | 954 ± 61.45 | <0.01 | 128 |
| C1 | Competitor Benchmark | 1475 ± 38.55 | 0.385 | 105 |

The bacterial ferment according to the invention exhibits a clear soothing effect by statistically significantly reducing the IL8 concentration in the supernatant by 39% compared to the stimulated control. Interestingly, the Raw Media Control (Culture broth prior to *Lactobacillus* fermentation) shows a pronounced irritating effect on the 3 models, whereas the Preservative Control as well as the Competitor Benchmark product both exhibit no modulation of IL8 concentration.

Modulation of Skin Moisture

The ability of the bacterial ferment according to the invention to influence and improve skin moisture was assessed in a clinical trial with water as the placebo. The study was conducted over a period of two weeks in a randomized, comparative design using blinded test samples. 22 female study subjects (age range 26-65 weeks) were selected in adherence to the Helsinki declaration. Subjects with skin conditions, as well as pregnant and lactating women were excluded from the study. The subjects applied the test samples twice daily on the volar forearms after thorough washing of the forearms with 10% sodium lauryl ether sulphate, 4% NaCl in water.

Skin moisture was assessed doing corneometer measurements (using a CM 825 corneometer probe connected to a MDD4 (Multidisplay Device, Courage+Khazaka electronic GmbH)) in the treated area at the beginning (day 0) and the end (day 13) of the application period. The measurement principle is based on a non-invasive capacity determination of the skin, which is quantitatively correlated to the water content.

Results are displayed as the means over subjects in difference of corneometer units (·d13-d0)±standard abbreviation. Statistical significance of difference of treatments was calculated vs untreated control using ANOVA (Tukey test). The results are shown in Table 3.

TABLE 3

Results skin moisture

| Ex. | Sample | Means of C.U. | ANOVA | p-value |
|---|---|---|---|---|
| | Untreated | −0.1 | 0.807 | — |
| | Placebo | 1.6 | 0.741 | 0.43 |
| 6 | Bacterial ferment according to the invention | 3.0 | 0.676 | 0.029 |

As shown in Table 3, the bacterial ferment according to the invention causes a significant increase in C.U., and thus in skin moisture content, over the 13d study duration.

Example 7

Reduction of *Lactobacillus* Viability by Treatment with Lactic Acid

To determine efficacy of the lactic acid treatment for reduction of *Lactobacillus* viability, a series of concentrations of lactic acid was added to *Lactobacillus* cultures. After 12 h incubation at 37° C. with stirring, pH of the samples was measured and *Lactobacillus* viability was determined by plating of serial dilutions for samples treated with lactic acid. The results are shown in Table 4:

TABLE 4

Effect of addition of various amounts of lactic acid on pH of the broth and bacterial count after incubation at 37° C. for 12 h

| Lactic Acid (% (w/v) | pH after 12 hrs | *Lactobacillus* count (log cfu/ml) |
|---|---|---|
| 0 | 7.14 | 9.90 |
| 2 | 4.56 | 7.54 |
| 2.8 | 5.56 | 7.08 |
| 3 | 4.17 | 5.45 |
| 3.4 | 4.56 | 4.72 |
| 3.6 | 4.08 | 5.09 |
| 4 | 3.94 | 3.52 |
| 4.4 | 3.88 | 3.60 |
| 4.8 | 3.83 | 3.00 |
| 5 | 3.75 | 1.00 |
| 5.4 | 3.78 | 1.38 |
| 6 | 3.65 | 1.95 |
| 6.8 | 3.56 | 1.70 |

As shown in Table 4, addition of lactic acid had a drastic effect on the viability of *Lactobacillus* cultures. Bacterial counts dropped rapidly with increasing amounts of lactic acid; the optimal reduction of *Lactobacillus* count was reached in a concentration range of ca. 5% (w/v) lactic acid.

Formulation Examples

In the following, the invention is illustrated by the following formulation examples 1 to 15. The amounts are indicated as % by weight for all formulations.

TABLE 1

Deodorant Spray with ACH

| Ingredients | EU INCI | Amount |
|---|---|---|
| Tri ethylcitrate | Triethyl citrate | 3.0 |
| Solubilizer ® | PEG-40 Hydrogenated Castor Oil, Trideceth-9, Propylene Glycol, Aqua | 1.0 |
| Ethanol 96% | Ethanol | 30.0 |
| Ethylhexylglycerin | Ethylhexylglycerin | 0.3 |
| SymDeo ® B125 | 2-Methyl 5-Cycloheylpentanol | 0.25 |
| SymClariol ® | Decylene Glycol | 0.25 |
| Frescolat ® ML | Menthyl Lactate | 0.6 |
| Tego ® Cosmo P 813MB | Polyglyceryl-3 Caprylate | 0.5 |
| Locron ® L (50%) | Aqua, Aluminum Chlorohydrate | 25.0 |
| Perfume oil PO1, PO2, PO3, PO4, or PO5 | Parfum | 0.5 |
| Water, demin. | Aqua | Add 100 |
| Bacterial ferment according to the invention | Lactobacillus Ferment, Ammonium Lactate, Lactic Acid, Pentylene Glycol | 5.0 |

TABLE 2

Deodorant Roll-on

| Ingredients | EU INCI | Amount |
|---|---|---|
| Aqua/Water | Aqua | Add 100 |
| Bacterial ferment according to the invention | Lactobacillus Ferment, Ammonium Lactate, Lactic Acid, Pentylene Glycol | 5.0 |
| Hydrolite ® CG | Caprylyl Glycol | 0.3 |
| SymSave ® H | Hydroxyacetophenone | 0.5 |
| EDTA NA2 | Disodium EDTA | 0.1 |
| Dracorin ® GOC | Glyceryl oleate citrate; Caprylic/Capric triglyceride | 4.0 |
| Dragoxat ® 89 | Ethyl hexyl isononanoate | 5.0 |
| SymMollient ® S green | Cetearyl Nonanoate | 1.0 |
| Genuvisco ® CG 131 | Carrageenan | 0.5 |
| Potassium Sorbate | Potassium Sorbate | 0.5 |
| Farnesol | Farnesol | 0.3 |
| Perfume oil PO1, PO2, PO3, PO4, or PO5 | Perfume | 1.0 |
| SymGuard ® CD | Phenylpropanol, o-Cymen-5-ol, Decylene Glycol | 0.3 |
| Sodium Hydroxide, 50% solution | Aqua; Sodium hydroxide | 0.2 |

TABLE 3

Flash SOS Face Gelee

| Ingredients | EU INCI | Amount |
|---|---|---|
| Dracorin ® GOC | Glyeryl Oleate Citrate, Caprylic/Capric Triglyceride | 0.6 |
| SymMollient ® PDCC | Propanediol Dicaprylate/Caprate | 6.0 |
| Dragoxat ® 89 | Ethylhexyl Isononanoate | 5.0 |
| PCL-Liquid ® 100 | Cetearyl Ethylhexanoate | 1.5 |
| Frescolat ® X-Cool | Menthyl Ethylamido Oxalate | 1.0 |
| Sym Relief ® 100 | Bisabolol, Zingiber Officinale Root Extract | 0.1 |
| Sym Decanox ™ HA | Caprylic/Capric Triglyceride, Hydroxymethoxyphenyl Decanone | 0.8 |
| Alpha Tocopherol DL | Tocopherol | 0.1 |
| Carbopol ® Ultrez 20 Polymer | Acrylates/C10-30 Alkyl Acrylate Crosspolymer | 0.4 |
| Aqua/Water | Aqua | Add 100 |
| Glycerin | Glycerin | 3.0 |
| SymMollient ® W/S | Trideceth-9, PEG-5 Isononanoate, Aqua | 1.0 |
| SymDiol ® 68 | 1,2-Hexanediol, Caprylyl Glycol | 0.5 |
| SymSave ® H | Hydroxyacetophenone | 0.5 |
| Bacterial ferment according to the invention | Lactobacillus Ferment, Ammonium Lactate, Lactic Acid, Pentylene Glycol | 20.0 |
| Aloe Vera Gel Concentrate | Aloe Barbadensis Leaf Juice | 1.5 |
| Sodium Hydroxide 10% solution | Aqua, Sodium hydroxide | 0.7 |
| Perfume oil PO1, PO2, PO3, PO4, or PO5 | Parfum | 0.5 |
| Color | | 0.03 |

TABLE 4

Intimate Sensi-Gel

| Ingredients | EU INCI | Amount |
|---|---|---|
| Aqua/Water | Aqua | Add 100 |
| Sodium Benzoate | Sodium benzoate | 0.3 |
| Keltrol ® CG-T | Xanthan Gum | 0.2 |
| Cyamopsis Tetragonolobus Gum | Cyamopsis Tetragonolobus Gum | 0.1 |
| Glycerin | Glycerin | 4.0 |
| Bacterial ferment according to the invention | Lactobacillus Ferment, Ammonium Lactate, Lactic Acid, Pentylene Glycol | 5.0 |
| Tego ® Betain F50 | Cocamidopropyl betaine | 14.0 |
| Solubilizer | PEG-40 Hydrogenated castor oil, Trideceth-9, Propylene Glycol, Aqua | 3.0 |
| Hydrolite ® 6 | 1,2 Hexanediol | 1.0 |
| SymGuard ® CD | Phenylpropanol, o-cymen-5-ol, Decylene Glycol | 0.3 |
| Sym Relief ® 100 | Bisabolol, Zingiber officinale root extract | 0.1 |
| Perfume oil PO1, PO2, PO3, PO4, or PO5 | Parfum | 0.2 |
| Frescolat ® X-cool | Menthyl ethylamido oxalate | 0.4 |
| Plantacare ® 2000 UP | Decyl Glucoside | 2.0 |
| Lactic acid 90% Nat. | Lactic Acid, Aqua | 0.3 |

TABLE 5

Cleansing Micellar Gel

| Ingredients | INCI | Amount |
|---|---|---|
| Water, distilled | Water (Aqua) | Ad 100 |
| Carbopol ® ETD2050 Polymer | Carbomer | 0.7 |
| Bacterial ferment according to the invention | Lactobacillus Ferment, Ammonium Lactate, Lactic Acid, Pentylene Glycol | 10.0 |
| SymOcide ® PS | Phenoxyethanol, Decylene glycol,1,2-hexanediol | 1.0 |
| Sodium Hydroxide 10% solution | Aqua, Sodium Hydroxide | 3.28 |
| SymMollient ® W/S | Trideceth-9, PEG-5 Isononanoate, Aqua | 1.0 |
| SymSol ® PF-3 | Aqua, Pentylene glycol, Sodium lauryl sulfoacetate, Sodium oleoyl sarcosinate, Sodium chloride, Sodium oleate | 3.0 |
| Perfume oil PO1; PO2; PO3; PO4 or PO5 | Parfum | 1.0 |
| SymVital ® AR | Zingiber officinale (ginger) root extract | 0.2 |

TABLE 5-continued

Cleansing Micellar Gel

| Ingredients | INCI | Amount |
|---|---|---|
| Extrapone ® Seaweed | Aqua, Butylene glycol, *Fucus vesiculosus* extract | 1.0 |
| Actipone ® Dandelion Juice (Organic) GW | *Glycerin Taraxacum officinale* juice Aqua | 1.0 |
| Colour I | Colour | 0.35 |
| Colour II | Colour | 0.20 |
| Caprylhydroxamic Acid | Caprylhydroxamic Acid | 0.2 |
| Phenylpropanol | Phenylpropanol | 0.2 |

TABLE 6

Aloe Shower Cream

| Ingredients | EU INCI | Amount |
|---|---|---|
| Water demin. | Water | Add 100 |
| Glycerin 85% | Glycerin, Water | 3.0 |
| Bacterial ferment according to the invention | *Lactobacillus* Ferment, Ammonium Lactate, Lactic Acid, Pentylene Glycol | 5.0 |
| Dermosoft ® 1388 ECO | Glycerin, Water, Sodium Levulinate, Sodium Anisate | 3.5 |
| Genuvisco ® CG-131 | Carrageenan | 0.8 |
| Keltrol ® CG-SFT | Xanthan Gum | 0.3 |
| Amisoft ® CS-22 | Sodium Cocoyl Glutamate, Disodium Cocoyl Glutamate, Water | 20.0 |
| Plantacare ® 2000 UP | Decyl Glucoside | 7.0 |
| *Aloe Vera* Gel Concentrate | *Aloe Barbadensis* Leaf Juice | 1.5 |
| SymOleo ® Vita 7 | *Glycine Soja* (Soybean) Oil, *Gossypium Herbaceum* (Cotton) Seed Oil, *Mangifera Indica* (Mango) Seed Butter, *Olea Europaea* (Olive) Fruit Oil, *Persea Gratissima* (Avocado) Oil, *Prunus Amygdalus Dulcis* (Sweet Almond) Oil, *Theobroma Cacao* (Cocoa) Seed Butter | 5.0 |
| Citric acid solution 10% | Aqua, citric acid | 6.7 |
| Perfume oil PO1, PO2, PO3, PO4, or PO5 | Parfum | 0.4 |
| Cosmopheres ® GYAM-M | Mannitol, Microcrystalline Cellulose, *Aloe Barbadensis* Leaf Juice Powder, Chromium Oxides greens, Iron Oxides | 2.0 |

TABLE 7

Fresh Hair shampoo

| Ingredients | EU INCI | Amount |
|---|---|---|
| Aqua | Aqua | Add 100 |
| EDTA B Powder | Disodium EDTA | 0.1 |
| Nativacare ™ 5600 | *Zea Mays* (Corn Starch) | 2.0 |
| Rheocare ® XGN | Xanthan Gum | 0.5 |
| Texapon ® NSO UP | Sodium Laureth sulfate | 35.0 |
| Dehyton ® K | Cocamidopropyl betaine | 8.0 |
| Plantacare ® 2000 UP | Decyl Glucoside | 4.0 |
| Perfume oil PO1, PO2, PO3, PO4, or PO5 | Parfum | 1.0 |
| SymSave ® H | Hydroxyacetophenone | 0.5 |
| Hydrolite ® 6 | 1,2-Hexanediol | 1.0 |
| SymClariol ® | Decylene Glycol | 0.3 |
| Frescolat ® ML cryst | Menthyl Lactate | 1.0 |
| SymCalmin ® | Pentylene Glycol, Butylene Glycol, Hydroxyphenyl propamidobenzoic acid | 0.2 |
| Crinipan ® AD | Climbazole | 0.2 |
| Propylene Glycol | Propylene Glycol | 2.0 |
| Bacterial ferment according to the invention | *Lactobacillus* Ferment, Ammonium Lactate, Lactic Acid, Pentylene Glycol | 5.0 |
| SymHair ® Shield | Pentylene Glycol, Aqua, *Glycerin*, *Triticum vulgare bran* extract, 1,2-Hexanediol, Capryly glycol | 1.0 |
| Sodium Hydroxide 10% solution | Aqua, Sodium hydroxide | 2.2 |

TABLE 8

Hair conditioner with UV protection

| Ingredients | INCI | Amount |
|---|---|---|
| Renex ™ PEG 6000 | PEG-150 | 2.5 |
| Hair Conditioner Base | Cetyl alcohol, behentrimonium chloride, *Triticum Vulgare* (Wheat) bran extract, linoleic acid | 3.0 |
| PCL-Solid | Stearyl heptanoate, stearyl caprylate | 0.5 |
| Dowsil ™ 5200 | Laurylmethicone copolyol | 0.5 |
| Natrosol ™ 250 HR | Hydroxyethylcellulose | 0.5 |
| Benzophenone-4 | Benzophenone-4 | 1.0 |
| Neo Heliopan ® AP | Disodiumphenyldibenz-imidazole tetrasulphonate | 1.0 |
| Amino methyl propanol | Amino methyl propanol | 2.0 |
| Xiameter ® 949 MEM-0949 Emulsion | Amodimethicone, cetrimonium chloride, trideceth-12 | 2.0 |
| Perfume oil PO1, PO2, PO3, PO4, or PO5 | Parfum | 0.8 |
| Hydrolite ® 6 | 1,2-Hexanediol | 0.5 |
| Bacterial ferment according to the invention | *Lactobacillus* Ferment, Ammonium Lactate, Lactic Acid, Pentylene Glycol | 5.0 |
| Water | Water (Aqua) | Add 100 |

TABLE 9

Low Cost-Refreshing Body Lotion

| Ingredients | EU INCI | Amount |
|---|---|---|
| Aqua/Water | Aqua | Add 100 |
| Bacterial ferment according to the invention | *Lactobacillus* Ferment, Ammonium Lactate, Lactic Acid, Pentylene Glycol | 10.0 |
| Extrapone ® Camomile | Aqua, Propylene Glycol, Butylene Glycol, *Chamomilla recutita*, (Matricaria) Flower extract, Bisabolol | 1.0 |
| Amaze ® XT | Dehydroxanthan Gum | 0.7 |
| Avicel ® PC591 | Cellulose, Cellulose Gum | 0.3 |
| Caprylic/Capric Triglyceride | Caprylic/Capric Triglyceride | 5.0 |
| Dragoxat ® 89 | Ethylhexyl Isononanoate | 3.0 |
| Dracorin ® GOC | Glyceryl Oleate Citrate, CaprylicCapric Triglyceride | 0.3 |
| Ethanol 96% | Alcohol denat. | 5.0 |
| Frescolat ® ML | Menthyl Lactate | 0.3 |
| Perfume oil PO1, PO2, PO3, PO4, or PO5 | Parfum | 0.2 |
| Sodium Hydroxide 10% solution | Aqua, Sodium hydroxide | 0.1 |
| SymOcide PS | Phenoxyethanol, Decylene Glycol, 1,2 Hexanediol | 1.0 |

TABLE 10

Anti-aging Face Cream, soft touch

| Ingredients | EU INCI | Amount |
|---|---|---|
| Aqua/Water | Aqua | Add 100 |
| Glycerin 99.5% | Glycerin | 2.0 |
| Dragosine ® | Carnosine | 0.1 |
| Kelcogel ® CG-HA | Gellan Gum | 0.1 |
| Keltrol ® CG-SFT | Xanthan Gum | 0.4 |
| Dracorin ® CE | Glyceryl Stearate Citrate | 2.0 |
| Lanette ® O | Cetearyl Alcohol | 5.0 |
| SymMollient ® PDCC | Propanediol Dicaprylate/Caprate | 3.0 |
| SymMollient ® S green | Cetearyl Nonanoate | 2.0 |
| Plantoil Triglyceride | Caprylic/Capric Triglyceride | 8.0 |
| Dragoxat ® 89 | Ethylhexyl Isononanoate | 2.0 |
| SymFinity ® 1298 | *Echinacea Purpurea* Extract | 0.1 |
| LIFTONIN XPERT Eco | Water, Mannan, Pentylene Glycol, Citric Acid | 2.0 |
| Bacterial ferment according to the invention | Lactobacillus Ferment, Ammonium Lactate, Lactic Acid, Pentylene Glycol | 20.0 |
| Perfume oil PO1, PO2, PO3, PO4, or PO5 | Parfum | 0.3 |

TABLE 11

Erythema Cotton Cream

| Raw material/Ingredients | INCI | Amount |
|---|---|---|
| Dehymuls ® PGPH | Polyglyceryl-2 Dipolyhydroxystearate | 5.25 |
| Tegosoft ® MM | Myristyl Myristate | 1.00 |
| Cacao Butter | Theobroma Cacao Seed Butter | 0.50 |
| Caprylic/Capric Triglyceride | Caprylic/Capric Triglyceride | 5.00 |
| Alpha Tocopherol DL | Tocopherol | 0.10 |
| Jojoba Oil | Simmondsia Chinensis Seed Oil | 10.00 |
| Bentone Gel ® GTCCV | Caprylic/Capric Triglyceride, Stearalkonium Hectorite, Propylene Carbonate | 2.50 |
| Sweet Almond Oil (Organic) | *Prunus Amygdalu Dulcis* (Sweet Almond) Oil | 10.00 |
| Cutina ® HR | Hydrogeated Castor Oil | 2.50 |
| Zinc Oxide | Zinc Oxide | 1.20 |
| Cetiol ® SB 45 | *Butyrospermum Parkii* Butter | 0.50 |
| Sym Decanox ™ HA | Caprylic/Capric Triglyceride, Hydroxymethoxyphenyl Decanone | 1.00 |
| Aqua/Water | Aqua | Add 100 |
| Magnesium Sulfate Heptahydrate | Magnesium Sulphate Hepta Hydrate | 0.50 |
| Glycerin | Glycerin | 5.00 |
| SymOcide ® PS | Phenoxyethanol, Decylene Glycol, 1,2 Hexanediol | 1.00 |
| Hydrolite ® 5 green | Pentylene Glycol | 1.00 |
| Bacterial ferment according to the invention | *Lactobacillus* Ferment, Ammonium Lactate, Lactic Acid, Pentylene Glycol | 5.00 |
| SymGlucan ® | Aqua, Glycerin, 1,2-Hexanediol, Caprylyl Glycol, Beta-Glucan | 5.00 |
| Extrapone ® Cotton Milk P | Glycerin, Aqua, PEG-40 Hydrogenated Castor Oil, Trideceth-9, Nonfat Dry Milk (Sine Adipe Lac), *Gossypium Herbaceum* Seed oil, 1,2 Hexanediol, Caprylyl Glycol | 1.00 |
| DragoCalm ® | Aqua, Glycerin, *Avena Sativa* Kernel Extract | 1.00 |
| Perfume oil PO1; PO2; PO3; PO4; or PO5 | Parfum | 0.05 |

TABLE 12

Natural Night Cream

| Raw material/Ingredients | INCI | Amount |
|---|---|---|
| Deionised Water | Aqua | Add 100 |
| Glycerin 99.5% | Glycerin | 2.0 |
| Dermofeel PA-3 | Sodium Phytate; Aqua; Alcohol | 0.1 |
| Dermosoft 1388 eco | Glycerin, Aqua, Sodium Levulinate, Sodium Anisate | 3.0 |
| Veegum Ultra Granules | Magnesium Aluminium Silicate | 0.5 |
| Keltrol CG-RD | Xanthan Gum | 0.5 |
| Dermofeel SL | Sodium Stearoyl Lactylate | 2.0 |
| Dermofeel PS | Polyglyceryl-3 Stearate | 3.0 |
| Dermosoft decalact MB | Sodium Caproyl/Lauroyl Lactylate | 0.8 |
| Phytosqualan, veg. grade | Squalane | 4.0 |
| Cegosoft SBE | *Butyrospermum Parkii* Butter; Tocopherol | 2.0 |
| Cutina GMS | Glyceryl Stearate | 2.0 |
| Lanette O | Cetearyl Alcohol | 1.0 |
| Sunflower oil | *Helianthus Annuus* Seed Oil | 4.0 |
| Dermofeel sensolv | Isoamyl Laurate | 5.0 |
| Bacterial ferment according to the invention | *Lactobacillus* Ferment, Ammonium Lactate, Lactic Acid, Pentylene Glycol | 20.0 |
| Perfume oil PO1; PO2; PO3; PO4; or PO5 | Parfum | 0.3 |

TABLE 13

Anti-Wrinkle Day Emulsion exp. SPF 15

| Raw material/Ingredients | INCI | Amount |
|---|---|---|
| Emulsiphos ® | Potassium cetyl phosphate, Hydrogenated palm glycerides | 2.5 |
| Neo Heliopan ® 303 | Octocrylene | 2.0 |
| Neo Heliopan ® OS | Ethylhexyl salicylate | 5.0 |
| Isoadipate | Diisopropyl adipate | 2.0 |
| SymMollient ® S green | Cetearyl nonanoate | 2.0 |
| Caprylic/Capric Triglyceride | Caprylic/capric triglyceride | 3.0 |
| Dragoxat ® 89 | Ethylhexyl isononanoate | 1.0 |
| PCL-Liquid ® 100 | Cetearyl ethyl hexanoate | 3.0 |
| SymUrban ® | Benzylidene dimethoxydimethylindanone | 0.3 |
| SymDecanox ™ HA | Caprylic/capric triglyceride Hydroxymethoxyphenyl decanone | 2.0 |
| Edeta ® BD | Disodium edta | 0.1 |
| Keltrol ® CG-SFT | Xanthan gum | 0.2 |
| Cosmedia ® SP | Sodium polyacrylate | 0.4 |
| Aqua/Water | Aqua | Add 100 |
| Glycerin | Glycerin | 3.0 |
| Neo Heliopan ® Hydro | Phenylbenzimidazole sulfonic acid | 2.0 |
| Biotive ® L-Arginine | Arginine | 1.0 |
| Sodium Hydroxide 10% solution | Aqua, Sodium hydroxide | 1.2 |
| Dragosine ® | Carnosine | 0.2 |
| SymSave ® H | Hydroxyacetophenone | 0.5 |
| SymDiol ® 68 ( | 1,2-hexanediol, Caprylyl glycol | 0.3 |
| Phenoxyethanol | Phenoxyethanol | 0.2 |
| Bacterial ferment according to the invention | *Lactobacillus* Ferment, Ammonium Lactate, Lactic Acid, Pentylene Glycol | 10.0 |
| SymLift ® | Aqua, Trehalose, Glycerin, Pentylene glycol, Beta-glucan, *Hordeum vulgare* seed extract, Sodium hyaluronate, 1,2-hexanediol, Caprylyl glycol | 5.0 |
| Macadamia Oil (refined) | *Macadamia integrifolia* seed oil | 0.2 |
| Ethanol 96% | Alcohol denat. | 3.0 |
| Sensocel ® 10 | Cellulose | 1.0 |
| Sipernat ® 11 PC | Hydrated silica | 1.0 |
| Perfume oil PO1; PO2; PO3; PO4; or PO5 | Parfum | 0.4 |

TABLE 14

Perfect Hand with exp. SPF 15, UVA/UVB Balanced

| Raw material/Ingredients | INCI | Amount |
|---|---|---|
| Emulsiphos ® | Potassium cetyl phosphate Hydrogenated palm glycerides | 1.5 |
| Lanette ® O | Cetearyl alcohol | 1.0 |
| Tegosoft ® MM | Myristyl myristate | 0.5 |
| Neo Heliopan ® OS | Ethylhexyl salicylate | 5.0 |
| Edeta ® BD | Disodium EDTA | 0.1 |
| Dragoxat ® 89 | Ethylhexyl isononanoate | 2.0 |
| Isoadipate | Diisopropyl adipate | 6.0 |
| PCL-Liquid ® 100 | Cetearyl ethylhexanoate | 3.0 |
| Corapan ® TQ | Diethylhexyl 2,6-naphthalate | 2.0 |
| Cetiol ® SB 45 | *Butyrospermum parkii* butter | 1.5 |
| SymBright ™ 2036 | Sclareolide | 0.2 |
| SymDecanox ™ HA | Caprylic/capric triglyceride, Hydroxymethoxyphenyl decanone | 1.0 |
| SymCare ® O | Hexyldecanol, Pentylene glycol, 4-t-butylcyclohexanol, Bisabolol, Cetylhydroxyproline palmitamide, Hydroxyphenyl propamidobenzoic acid, Stearic acid, *Brassica campestris* (rapeseed) sterols, *Zingiber officinale* (ginger) root extract | 2.0 |
| Genuvisco ® Carrageenan CG-131 | *Chondrus crispus* powder | 0.4 |
| Keltrol ® CG-SFT | Xanthan gum | 0.2 |
| Aqua/Water | Aqua | Add 100 |
| Neo Heliopan ® Hydro | Phenylbenzimidazole sulfonic acid | 2.5 |
| Biotive ® L-Arginine | Arginine | 1.0 |
| Sodium Hydroxide 10% solution | Aqua Sodium hydroxide | 1.3 |
| Glycerin | Glycerin | 2.0 |
| SymSave ® H | Hydroxyacetophenone | 0.5 |
| SymDiol ® 68 | 1,2-hexanediol, Caprylyl glycol | 0.5 |
| RonaFlair ® Flawless | Silica Ci 77892, Ci 77491 | 1.5 |
| Tego ® Feel C10 | Cellulose | 1.5 |
| Bacterial ferment according to the invention | *Lactobacillus* Ferment, Ammonium Lactate, Lactic Acid, Pentylene Glycol | 10.0 |
| Perfume oil PO1; PO2; PO3; PO4; or PO5 | Parfum | 0.5 |

What is claimed:

1. A bacterial ferment obtained by a method comprising the following steps:
    (a) culturing *Lactobacillus* species in at least one growth medium for at least 24 hours;
    (b) separating the mixture via centrifugation to obtain a supernatant;
    (c) adding lactic acid to the supernatant obtained from step b) in an amount sufficient to lower the pH value of the supernatant to obtain a resulting mixture, wherein the amount of lactic acid is from 2 to 10 percent, by weight, of the total amount of the mixture;
    (d) stabilizing the resulting mixture by adding at least one preservative and/or at least one multifunctional,
        wherein the at least one preservative comprises benzoic acid, or esters and salts thereof; propionic acid or salts thereof; salicylic acid or salts thereof; 2,4-hexanoic acid (sorbic acid) or salts thereof; formaldehyde, paraformaldehyde; 2-hydroxybiphenyl ether or salts thereof; 2-zincsulphidopyridine N-oxide; inorganic sulphites, inorganic bisulphites; sodium iodate; chlorobutanol; 4-hydroxybenzoic acid or salts or esters thereof; dehydroacetic acid; formic acid; 1,6-bis(4-amidino-2-bromophenoxy)-n-hexane or salts thereof; sodium salt of ethylmercury-(II)-thiosalicylic acid; phenylmercury or salts thereof; 10-undecylenic acid or salts thereof; 5-amino-1,3-bis(2-ethylhexyl)-5-methylhexahydropyrimidine; 5-bromo-5-nitro-1,3-dioxane; 2-bromo-2-nitro-1,3-propanediol; 2,4-dichlorobenzyl alcohol; N-(4-chlorophenyl)-N'-(3,4-dichlorophenyl)urea; 4-chloro-m-cresol; 2,4,4'-trichloro-2'-hydroxy-diphenyl ether; 4-chloro-3,5-dimethylphenol; 1,1'-methylene-bis(3-(1-hydroxymethyl-2,4-dioxoimidazolidin-5-yl)urea); poly(hexamethylene biguanide) hydrochloride; 2-phenoxyethanol; hexamethylenetetramine; 1-(3-chloroallyl)-3,5,7-triaza-1-azoniaadamantane chloride; 1-(4-chloro-phenoxy)-1(1H-imidazol-1-yl)-3,3-dimethyl-2-butanone; 1,3-bis(hydroxymethyl)-5,5-dimethyl-2,4-imidazolidinedione; benzyl alcohol; piroctone olamine; 1,2-dibromo-2,4-dicyanobutane; 2,2'-methylene-bis(6-bromo-4-chloro-phenol); bromochlorophene; mixture of 5-chloro-2-methyl-3 (2H)-isothiazolinone and 2-methyl-3(2H)isothiazolinone with magnesium chloride and/or magnesium nitrate; 2-benzyl-4-chlorophenol; 2-chloroacetamide; chlorhexidine; chlorhexidine acetate; chlorhexidine gluconate; chlorhexidine hydrochloride; 1-phenoxy-propan-2-ol; N-alkyl(C12-C22)trimethylammonium bromide and/or chloride; 4,4-dimethyl-1,3-oxazolidine; N-hydroxymethyl-N-(1,3-di(hydroxymethyl)-2,5-dioxoimidazolidin-4-yl)-N'-hydroxymethylurea; 1,6-bis(4-amidinophenoxy)-n-hexane or salts thereof; glutaraldehyde 5-ethyl-1-aza-3,7-dioxabicyclo(3.3.0)octane; 3-(4-chlorophenoxy)-1,2-propanediol; hyamine; alkyl (C8-C18)dimethylbenzylammonium chloride; alkyl (C8-C18)dimethylbenzylammonium bromide; alkyl (C8-C18)dimethylbenzylammonium saccharinate; benzylhemiformal; 3-iodo-2-propynyl butylcarbamate; or sodium ((hydroxymethyl)amino)acetate; and
        wherein the at least one multifunctional comprises 1,2-propanediol; 1,3-propanediol; 1,2-butanediol; 1,3-butanediol (butylene glycol); 1,2-pentanediol; 1,2-hexanediol; 1,2-heptanediol; 1,2-octanediol; 1,2-nonanediol; 1,2-decanediol; glycerol; phenoxyethanol; ethylhexylglycerin; glyceryl caprylate; hydroxyacetophenone; methylbenzyl alcohol; o-cymen-5-ol; benzyl alcohol; tropolone; or mixtures of two or more of said multifunctionals; and optionally
    (e) filtering the mixture to remove any final precipitation.

2. A composition comprising the bacterial ferment according to claim 1, wherein the composition is a pharmaceutical composition or a cosmetic composition.

3. The composition according to claim 2, wherein the composition is selected from the group consisting of oil in water emulsion, water in oil emulsion, crème, lotion, and ointment.

4. A product comprising the bacterial ferment according to claim 1, wherein the product is a pharmaceutical product or a cosmetic product.

* * * * *